(12) United States Patent
Toso et al.

(10) Patent No.: US 8,828,092 B2
(45) Date of Patent: Sep. 9, 2014

(54) REINFORCED MESH FOR RETROPUBIC IMPLANTS

(75) Inventors: Kenneth E. Toso, Westborough, MA (US); Jeffery V. Bean, Fitchburg, MA (US); Michael F. Weiser, Groton, MA (US); Doreen Rao, Sudbury, MA (US); Alan Fortunate, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1170 days.

(21) Appl. No.: 12/006,431

(22) Filed: Jan. 2, 2008

(65) Prior Publication Data

US 2008/0161837 A1 Jul. 3, 2008

Related U.S. Application Data

(60) Provisional application No. 60/878,311, filed on Jan. 2, 2007.

(51) Int. Cl.
*A61F 2/02* (2006.01)
*A61F 2/00* (2006.01)
*A61F 2/30* (2006.01)

(52) U.S. Cl.
CPC .......... *A61F 2/0045* (2013.01); *A61F 2/0077* (2013.01); *A61F 2250/0018* (2013.01); *A61F 2250/0026* (2013.01); *A61F 2002/30322* (2013.01)
USPC ...................................... 623/23.72

(58) Field of Classification Search
USPC ............... 606/213, 215, 37; 623/11, 15, 66, 623/23.72; 600/37
See application file for complete search history.

(56) References Cited

U.S. PATENT DOCUMENTS

| | | | |
|---|---|---|---|
| 6,648,921 B2 | 11/2003 | Anderson et al. | |
| 2002/0107430 A1 | 8/2002 | Neisz et al. | |
| 2003/0078468 A1 | 4/2003 | Skiba et al. | |
| 2003/0191360 A1 | 10/2003 | Browning | |
| 2004/0015048 A1 | 1/2004 | Neisz et al. | |
| 2005/0038452 A1 | 2/2005 | Chu | |
| 2006/0195010 A1 | 8/2006 | Arnal et al. | |
| 2006/0195011 A1 * | 8/2006 | Arnal et al. | 600/37 |
| 2007/0043255 A1 * | 2/2007 | O'Donnell | 600/30 |

FOREIGN PATENT DOCUMENTS

| | | |
|---|---|---|
| WO | WO-03/086205 | 10/2003 |
| WO | WO-03096929 | 11/2003 |
| WO | WO-2005/122954 | 12/2005 |
| WO | WO 2005122954 A1 * | 12/2005 |

OTHER PUBLICATIONS

Office Action for CA Application No. 2,734,026, mailed Feb. 25, 2014, 3 pages.

* cited by examiner

*Primary Examiner* — Gregory Anderson
*Assistant Examiner* — Christina Lauer

(57) ABSTRACT

Disclosed are reinforced meshes for retropubic implants for treatment of urinary incontinence and/or pelvic floor disorders and related uses, devices, and methods. In certain embodiments, implants have various resilient strengthening members added to a retropubic support mesh.

16 Claims, 30 Drawing Sheets

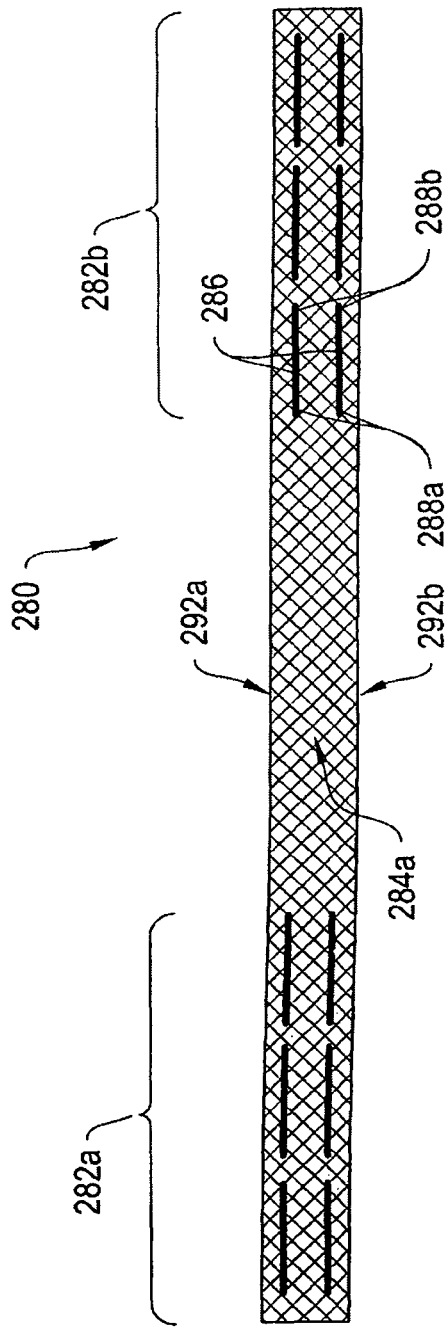
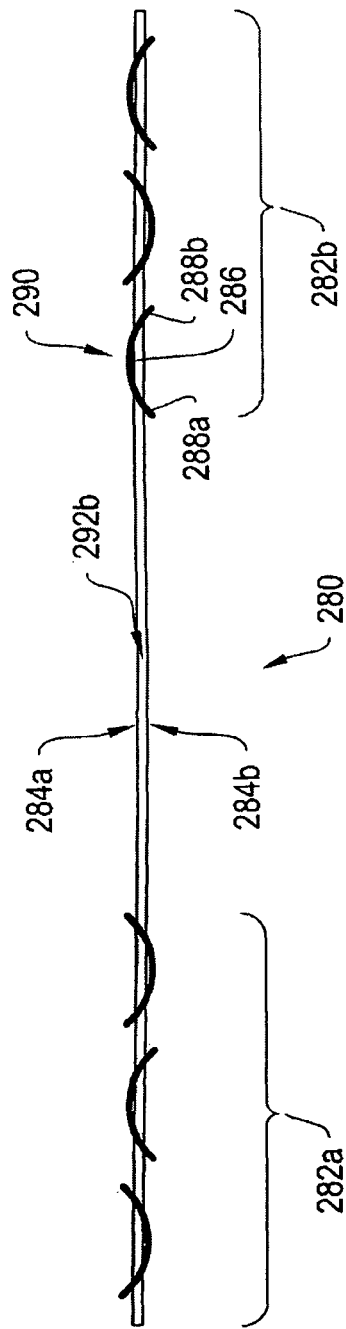
Figure 9A
Figure 9B

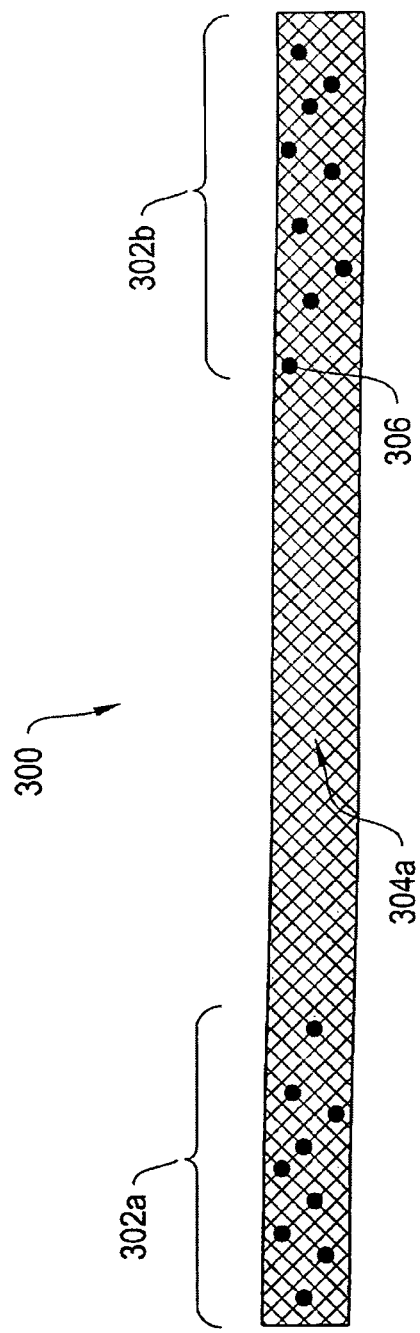
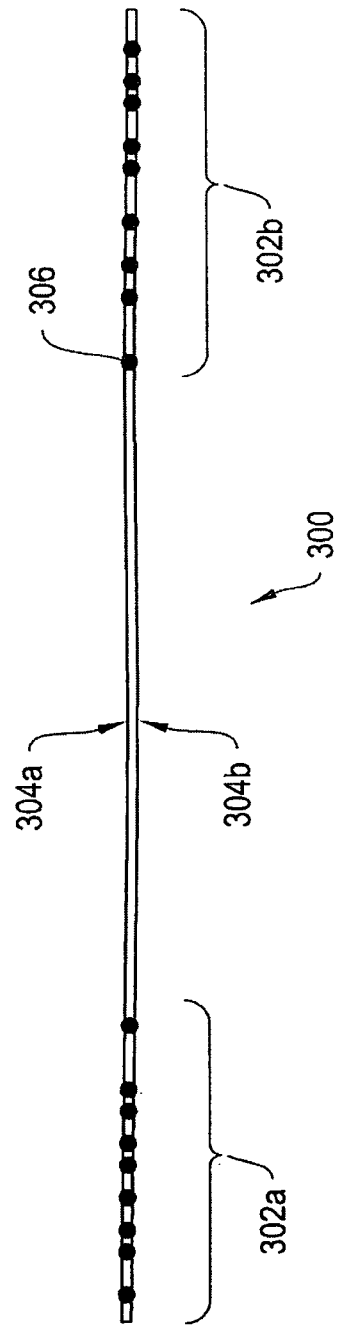
Figure 10A
Figure 10B

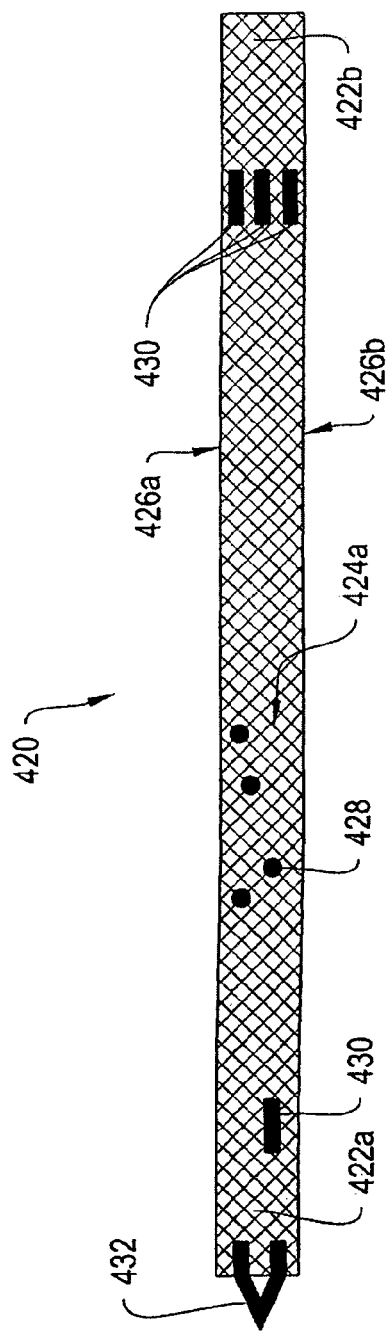
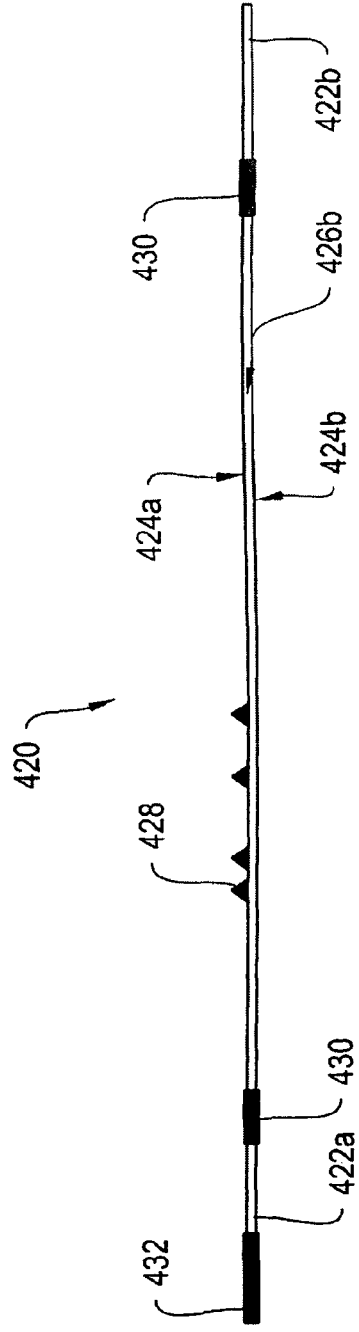

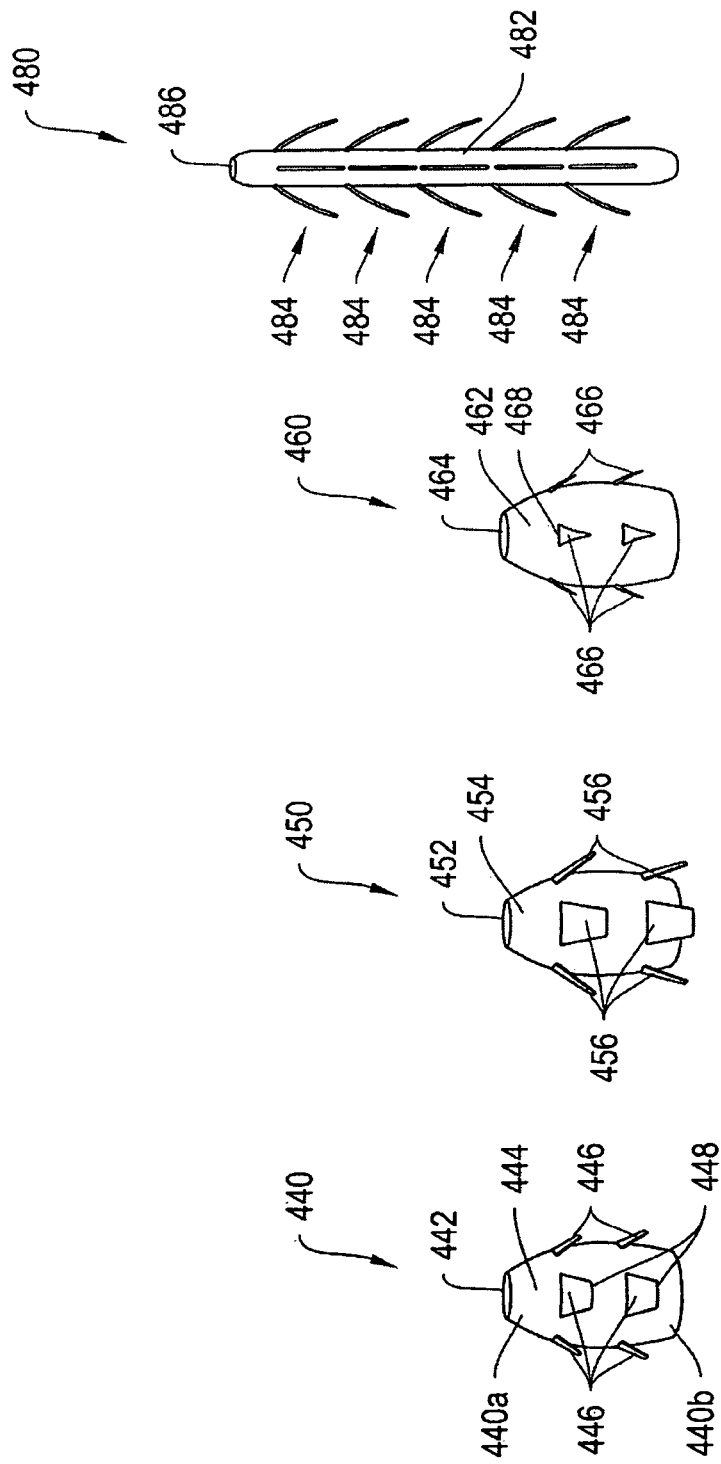

REINFORCED MESH FOR RETROPUBIC IMPLANTS

RELATED APPLICATIONS

This application claims the benefit of U.S. Provisional Application Ser. No. 60/878,311, filed Jan. 2, 2007 and titled "Reinforced Mesh for Retropubic Implants," the entire contents of which are incorporated herein by reference.

BACKGROUND

Pelvic floor disorders are a class of abnormalities that affect the pelvic region of patients, and they afflict millions of women. The pelvic region includes various anatomical structures such as the uterus, the rectum, the bladder, and the vagina. These anatomical structures are supported and held in place by a complex collection of tissues, such as muscles and ligaments. When these tissues are damaged, stretched, or otherwise weakened, the anatomical structures of the pelvic region shift and in some cases protrude into other anatomical structures. For example, when the tissues between the bladder and the vagina weaken, the bladder may shift and protrude into the vagina, causing a pelvic floor disorder known as cystocele. Other pelvic floor disorders include vaginal prolapse, vaginal hernia, rectocele, enterocele, uterocele, and/or urethrocele.

Pelvic floor disorders often cause or exacerbate female urinary incontinence (UI). One type of UI, called stress urinary incontinence (SUI), effects primarily women and is often caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged. When the afflicted woman sneezes, coughs, or otherwise strains the pelvic region, the bladderneck and proximal urethra rotate and descend. As a result, the urethra does not close with sufficient response time, and urine leaks through the urethra. Often, treatments of stress incontinence are made without treating the pelvic floor disorders at all, potentially leading to an early recurrence of the stress incontinence.

UI and pelvic floor disorders, which are usually accompanied by significant pain and discomfort, are often treated by implanting a supportive sling in or near the pelvic floor region to support the fallen or shifted anatomical structures or more generally, to strengthen the pelvic region by promoting tissue ingrowth. Such slings may be made from a variety of materials, but are often made from a mesh material. A mesh may be placed, for example, under the urethra, close to the high-pressure zone with little or no elevation to the urethra. When abdominal pressure increases, such as from coughing, sneezing, or the like, the sling facilitates the collapse of the urethra as a mechanism for closing the urethra to inhibit urine leakage. As another example, a wider mesh may be placed under the bladder to prevent it from protruding into other anatomical structures such as the vagina.

Various methods exist for implanting and securing slings. Some methods use soft tissue anchors to secure the slings to specific locations within the patient. These methods require highly accurate sling length to insure the sling aligns with the appropriate anchoring locations while creating the correct balance of tension and slack under the urethra or prolapsed organ. Some securement methods rely on the intrinsic coarseness of the edges of the mesh material to adhere to the patient's tissue, requiring the sling to have a substantial length. However, many current procedures, such as transobturator (TOT) and single incision procedures, require a shorter sling.

After the sling is implanted, the mesh material of the sling stretches and becomes less resilient, losing its ability to collapse the urethra or support the prolapsed organ. Scar tissue may form around the sling, further securing the sling within the patient and facilitating urethral closure or prolapsed organ support, but the scar tissue formation may be impeded by the stretching of the mesh. Previous methods for strengthening the sling typically reduced or did not address the sling's ability to be secured within the patient.

There is need for a sling with prolonged mesh material resilience, improved stimulation of scar tissue ingrowth, and a stronger securement method that is less dependent on sling length.

SUMMARY

The invention relates generally to systems and methods for improving the retention, resilience, and strength of surgically implantable supportive implants for use in treating urinary incontinence and/or pelvic floor conditions in a patient. More specifically, in various embodiments, the invention is directed to mesh implants featuring various resilient strengthening members added to a retropubic support mesh. These members may adhere to the patient's suburethral or pelvic floor tissues, reinforce the mesh material, stimulate scar tissue ingrowth, or some combination thereof. Moreover, these members may obviate the need for an anchor and allow for the use of a relatively short mesh length. In one respect, the invention includes an implant adapted to support a patient's pelvic or retropubic tissues. The implant includes a mesh having at least one longitudinal edge and at least one longitudinal surface and being sized and shaped to support one or more of a patient's urethra, bladderneck, and pelvic organ; and a resilient strengthening member disposed within or on the mesh and protruding beyond one or more of a longitudinal edge and a longitudinal surface.

In certain embodiments, the resilient strengthening member protrudes beyond a first longitudinal edge of the mesh and a second longitudinal edge of the mesh. The resilient strengthening member can also attach to the mesh at a plurality of points. In certain embodiments, the resilient strengthening member is a rigid member having a portion adapted to penetrate a tissue of a patient. In certain embodiments, the resilient strengthening member is fibrous and/or is one or more of composite plastic or metal. The rigid member can be shaped as desired, and may be curved, spherical, bulky, oblong, or otherwise shaped. The rigid member can be disposed obliquely with respect to the longitudinal edge, substantially perpendicular to the longitudinal edge, or substantially parallel to the longitudinal edge. The resilient strengthening member can include a rigid member deposited on a surface of the mesh.

In certain embodiments, the mesh is configured in an irregular shape for pelvic organ support, and can include one or more securement straps, where at least one of the one or more securement straps includes a resilient strengthening member disposed in an end region of the securement strap. An end region of the mesh may be configured in an irregular shape for securing to a location within the patient. In certain embodiments, the resilient strengthening member is disposed in an end region of the mesh. The resilient strengthening member may be disposed inward from an end edge of the mesh and/or at least about 25% of a way from an end of the mesh to a center of the mesh. The resilient strengthening member may also be spaced away from a center region of the mesh, where the center region is adapted to be adjacent to one or more of the patient's urethra, bladderneck, and pelvic organ.

In certain embodiments, the implant includes an anchor disposed at an end of the mesh for securing the implant to soft tissue within a patient. The mesh can include one or more regions having tangs that project from a longitudinal edge.

In certain embodiments, the implant includes a plurality of resilient strengthening members. The implant may further include a first plurality of resilient strengthening members disposed in a first end region of the mesh and a second plurality of resilient strengthening members disposed in a second end region of the mesh. In certain implementations, two or more resilient strengthening members directly connect and may be affixed to each other. In certain embodiments, at least one resilient strengthening member couples to a plurality of other resilient strengthening members.

In another aspect, the invention includes methods for implanting a surgical implant in the retropubic space or other region of a patient's pelvic floor. In one exemplary method, the operation creates an incision in the vaginal wall of the patient; couples an implant to a delivery device, wherein the implant is a mesh implant having a longitudinal edge, a longitudinal surface, and a resilient strengthening member disposed within or on the mesh implant and protruding beyond one or more of the longitudinal edge and the longitudinal surface; and inserts the delivery device through the vaginal incision via the external vaginal opening of the patient to extend a portion of the implant within the patient's pelvic region. In certain embodiments, the method also includes guiding the device to a location beneath the patient's epidermis to secure the implant in the patient's soft tissue. Transobtural, transabdominal, prepubic, suprapubic, and other methods may be used.

BRIEF DESCRIPTION OF THE FIGURES

Features and advantages of the invention will be more fully understood by the following illustrative description with reference to the appended drawings in which like elements are labeled with like reference designations and which may not be drawn to scale.

FIGS. 9A and 9B depict, respectively, a top view and a side view of an exemplary mesh incorporating stiffening members that protrude from surfaces of the sling of FIGS. 1A and 1B.

FIGS. 10A and 10B depict an exemplary mesh incorporating strengthening knots protruding from surfaces of the sling of FIGS. 1A and 1B.

FIGS. 15A and 15B depict, respectively, a top view and a side view of an exemplary mesh incorporating a plurality of resilient strengthening members disposed on and within the sling of FIGS. 1A and 1B.

FIGS. 16A-16E depict exemplary soft tissue anchors that may be used with the implants disclosed herein.

DETAILED DESCRIPTION OF CERTAIN EXEMPLARY EMBODIMENTS

The invention relates generally to systems and methods for improving the retention, resilience, and strength of surgically implantable supportive implants for use in treating urinary incontinence and/or pelvic floor conditions in a patient. More specifically, in various embodiments, the invention is directed to mesh implants featuring various resilient strengthening members added to a retropubic support mesh. These members may adhere to the patient's suburethral or pelvic floor tissues, reinforce the mesh material, stimulate scar tissue ingrowth, or some combination thereof. Moreover, these members may obviate the need for an anchor and allow for the use of a relatively short mesh length.

Figure 1A:
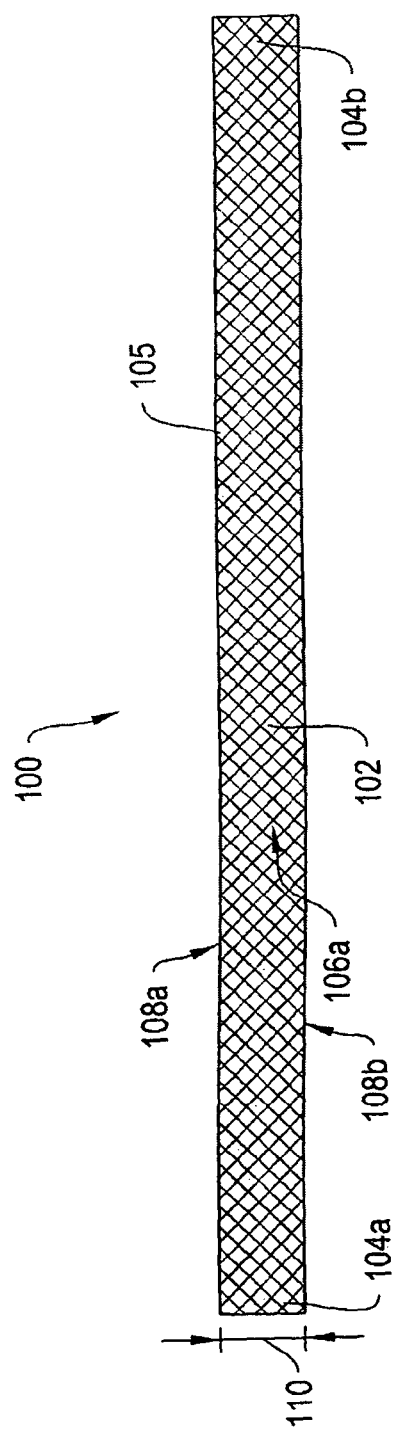
FIGS. 1A and 1B depict, respectively, a top view and a side view of a sling mesh.
Figure 1B:
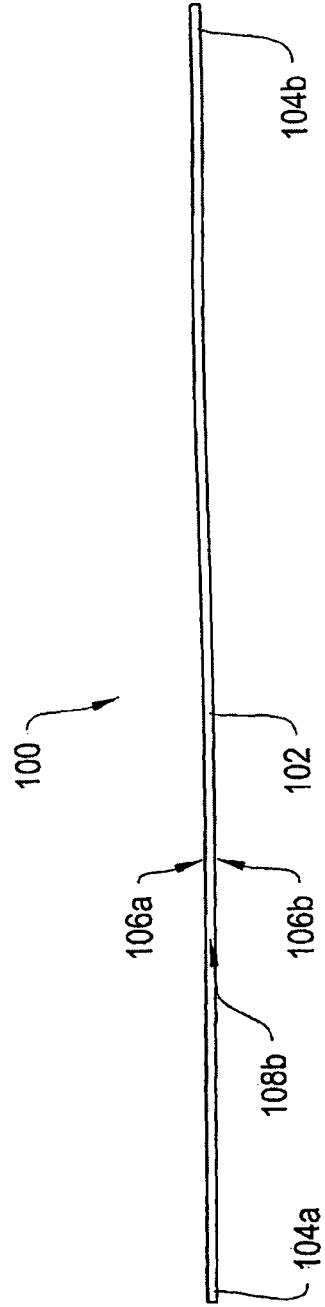

FIGS. 1A and 1B depict, respectively, a top view and a side view of a mesh 100 used in supportive slings for urethral support. The mesh shape has a center region 102, which may be configured to support the urethra and/or a prolapsed organ, surrounded by two opposing end regions 104a and 104b that are adapted to be implanted in a patient's tissue to hold the mesh in the pelvic region of the patient. The mesh 100 also has two longitudinal top and bottom surfaces 106a and 106b that are bounded by longitudinal edges 108a and 108b. The longitudinal edges 108a and 108b may have tangs, which in certain embodiments are ends of fibers of the mesh material, that project from the nominal longitudinal edges 108a and 108b of the mesh 100. The tangs may hook into and adhere to the patient's tissue or stimulate scar tissue ingrowth. The mesh material features a network of regularly spaced holes 105 that serve as a lattice upon which scar tissue may grow. Perpendicular to the length of the mesh 100 is a width 110. Both the width 110 and a length of the mesh 100 may be selected based on the specific anatomical structures being supported and the procedure for implanting the mesh 100. For example, the depicted mesh 100 can have a longitudinal length of between about 6 cm and about 15 cm to extend laterally between both of the patient's obturator foramen, and an anterior-to-posterior width 110 of between about 0.5 cm and about 2 cm to support the urethra and/or bladderneck. Longer or shorter lengths may be appropriate, depending on the procedure for implanting the mesh 100. Wide meshes may also be used in systems that support the bladder, uterus, rectum or other pelvic organ, as discussed below. Note that the fibers or other members that make up the mesh 100 may be obliquely oriented with respect to the length and width 110 of the mesh 100.

FIGS. 2-9B depict certain exemplary meshes incorporating various stiffening members in different orientations. As described, the stiffening members are disposed with respect to (and in certain embodiments secured to) the mesh material to help strengthen the mesh 100 depicted in FIG. 1 and may protrude in various orientations and arrangements to help hold the mesh 100 in place and stimulate scar tissue ingrowth. Suitable materials and methods for manufacturing stiffening members and attaching them to the mesh 100 are described below. Generally, a stiffening member is less elastic and less flexible than the mesh 100 (e.g., the strands or other members that are used to make the mesh), and may impart a relative rigidity to the part of the mesh 100 to which it is attached (e.g., because the stiffening member is attached to the mesh at several points along the length of the stiffening member). The stiffening members thereby help prevent significant stretching of the mesh 100.

FIGS. 2-4B depict exemplary meshes that incorporate straight stiffening members 128, 146, and 166 that lie in the plane of the mesh 100 depicted in FIG. 1, protrude from the longitudinal edges 108a and 108b, and are disposed in the end regions 104a and 104b of the mesh 100. Each straight stiffening member has longitudinal edge protrusions adapted to penetrate the patient's tissue to help secure the end regions 104a and 104b to the body and stimulate scar tissue ingrowth at the end regions 104a and 104b.

Figure 2:
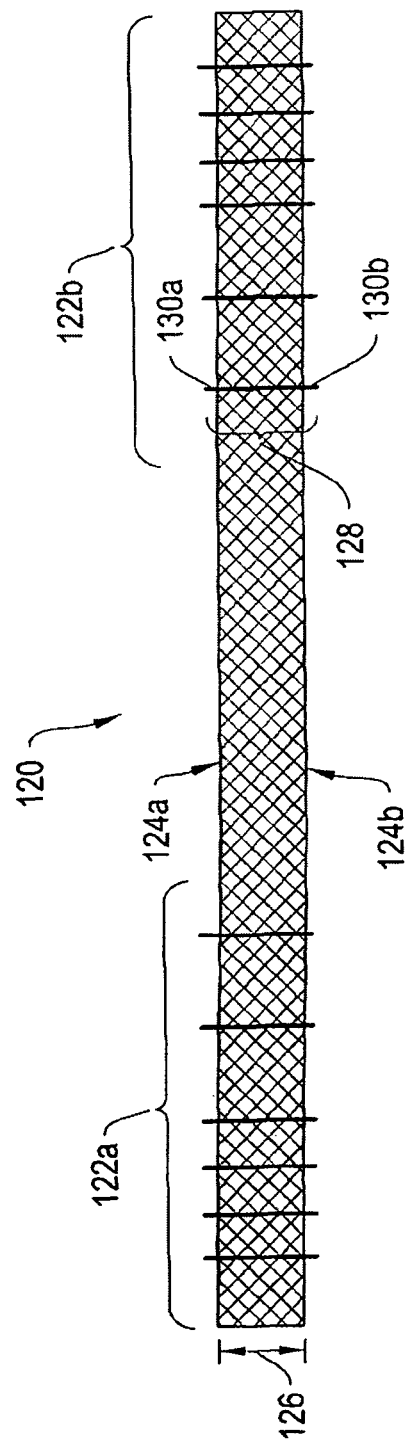
FIGS. 2, 3, 4A, and 4B depict various exemplary meshes incorporating stiffening members with the sling of FIGS. 1A and 1B.

FIG. 2 depicts an exemplary mesh 120 incorporating straight stiffening members 128 that are transverse to the longitudinal axis of the mesh 120 and arrayed at varying distances from one another. The straight stiffening members 128 each have longitudinal edge protrusions 130a and 130b adapted to penetrate the flesh to help secure end regions 122a and 122b of the mesh 120 to the body and stimulate scar tissue ingrowth at the end regions 122a and 122b. The straight stiffening members 128 are disposed in the end regions 122a and 122b, perpendicular to longitudinal edges 124a and 124b of the mesh 120 to help reduce the mesh's ability to stretch. In particular, for a diagonal mesh similar to mesh 100 depicted in FIG. 1, the width 110 of the mesh 100 typically narrows to allow the mesh 100 to lengthen. The straight stiffening members 128 help maintain a width 126 of the mesh 120 (e.g., because each stiffening member is secured to the mesh at several points along the length of the stiffening member), which may prevent significant stretching of the mesh 120.

Figure 3:
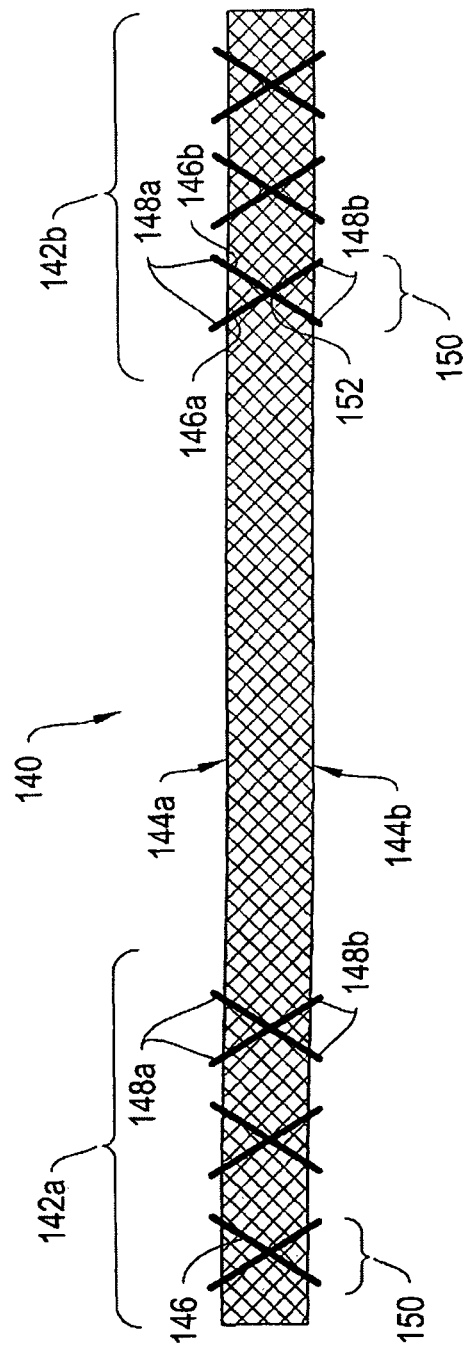

FIG. 3 depicts an exemplary mesh 140 incorporating straight stiffening members 146 arrayed in non-overlapping X shaped structures 150 uniformly spaced in each end region 142a and 142b of the mesh 140. Each X structure 150 has a "left" straight stiffening member 146a and a "right" straight stiffening member 146b which cross (and may optionally be secured together) at a crossing point 152 that lies substantially near the center of each straight stiffening member 146a and 146b. In other words, both stiffening members 146a and 146b in an X structure 150 are generally transverse to the longitudinal axis of the mesh 140, but neither is truly perpendicular to the axis. In addition, each stiffening member in the X structure 150 forms a different angle with the longitudinal axis. By orienting the straight stiffening members 146 along at least two different directions transverse to the longitudinal axis of the mesh 140, one direction generally parallel to the left straight stiffening member 146a and another direction generally parallel to the right straight stiffening member 146b, the mesh 140 may prevent significant stretching of the mesh 140 along either direction as well as along other directions. This feature is enhanced by securing each stiffening member 146 to the mesh 140 at several points along the length of the stiffening member 146. The straight stiffening members 146 are also oriented obliquely with respect to longitudinal edges 144a and 144b, allowing the longitudinal edge protrusions 148a and 148b to extend from the longitudinal edges 144a and 144b at acute angles which hook the end regions 142a and 142b into the flesh.

Figure 4A:
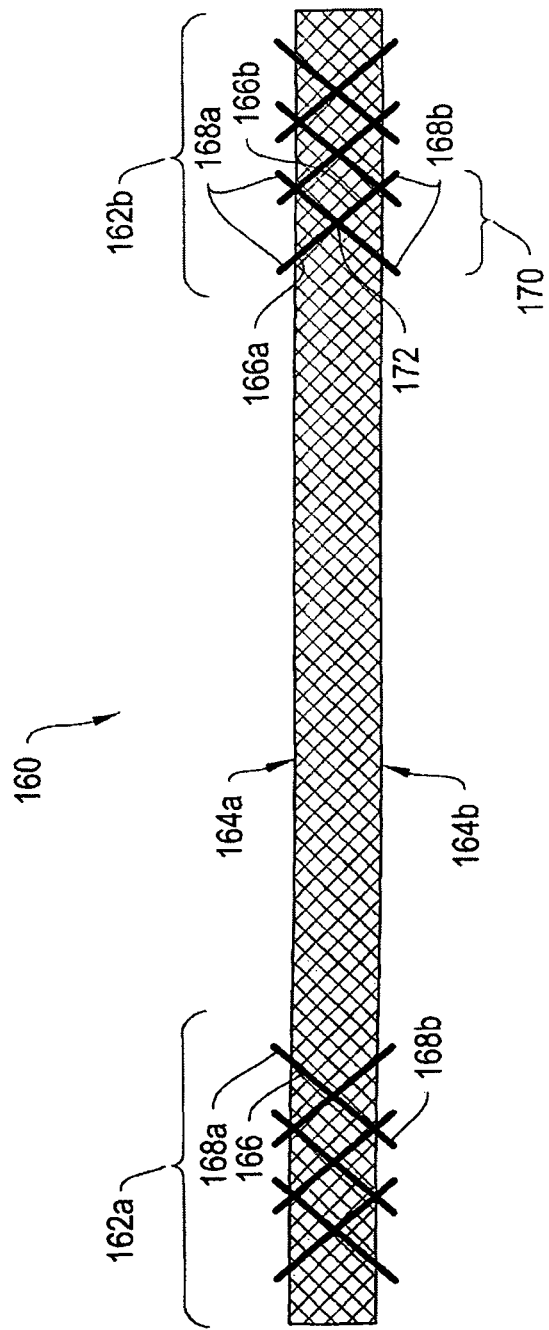

FIG. 4A depicts an exemplary mesh 160 incorporating straight stiffening members 166 arrayed in overlapping X structures 170 and disposed at each end region 162a and 162b of the mesh 160. Similar to each X structure 150 of FIG. 3, each X structure 170 has a "left" straight stiffening member 166a and a "right" straight stiffening member 166b which cross (and may optionally be secured together) at a crossing point 172 that lies substantially near the center of each straight stiffening member 166a and 166b. In contrast to FIG. 3, each X structure 170 of mesh 160 is configured to overlap with at least one other X structure 170 to increase the points on the mesh 160 that have contact (and are thus stabilized by) the straight stiffening members 166. Increasing the mesh's contact with straight stiffening members 166 may impart more strength and resilience to the mesh material.

Figure 4B:
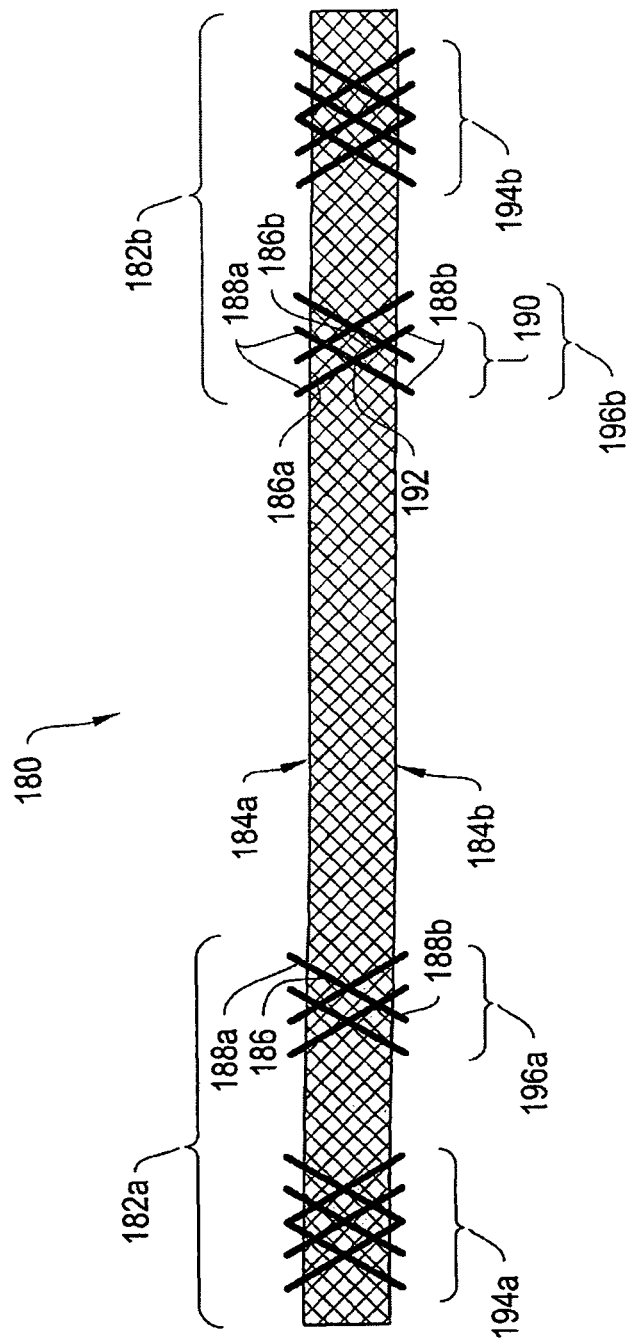

FIG. 4B depicts an exemplary mesh 180 incorporating straight stiffening members 186 disposed at each end region 182a and 182b of the mesh 180 and arrayed in overlapping X structures 190 similarly to members 166 of FIG. 4A. Similar to each X structure 170 of FIG. 4A, each X structure 190 has a "left" straight stiffening member 186a and a "right" straight stiffening member 186b which cross (and may optionally be secured together) at a crossing point 192 that lies substantially near the center of each straight stiffening member 186a and 186b. In contrast to FIG. 4A, the overlapping X structures 190 are configured to be relatively close and can form multiple regions 194a, 194b, 196a, and 196b of overlap within each end region 182a and 182b. In addition to further increasing the number of points on the mesh 180 that have contact with straight stiffening members 186, the configuration of mesh 180 can advantageously create a plurality of (and optimally, more than two) securement locations along the length of the mesh 180.

Figure 5:
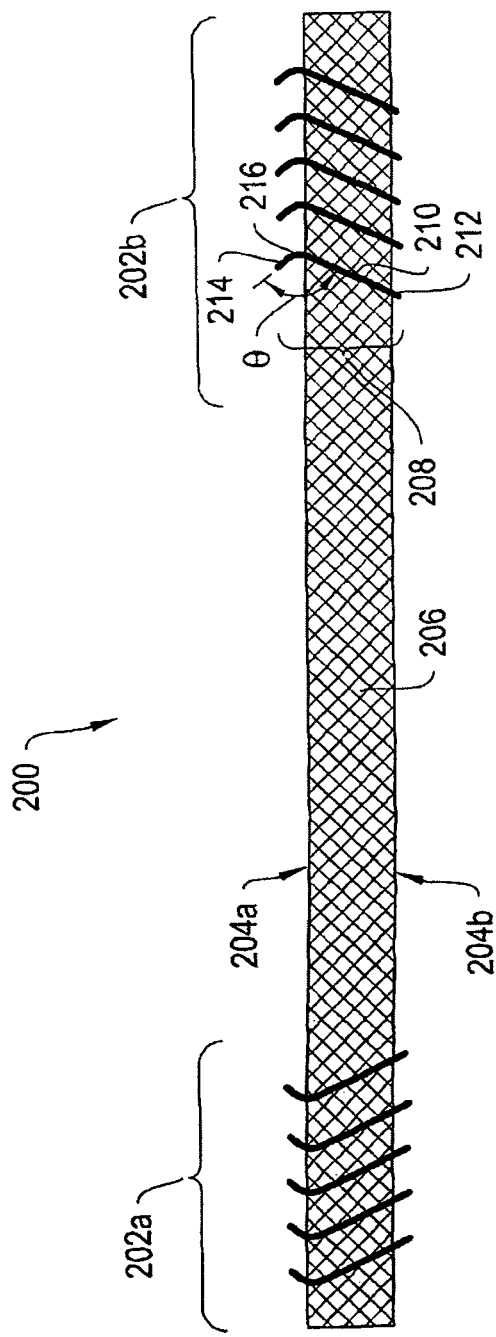
FIGS. 5 and 6 depict various exemplary meshes incorporating stiffening members with the sling of FIGS. 1A and 1B.
Figure 6:
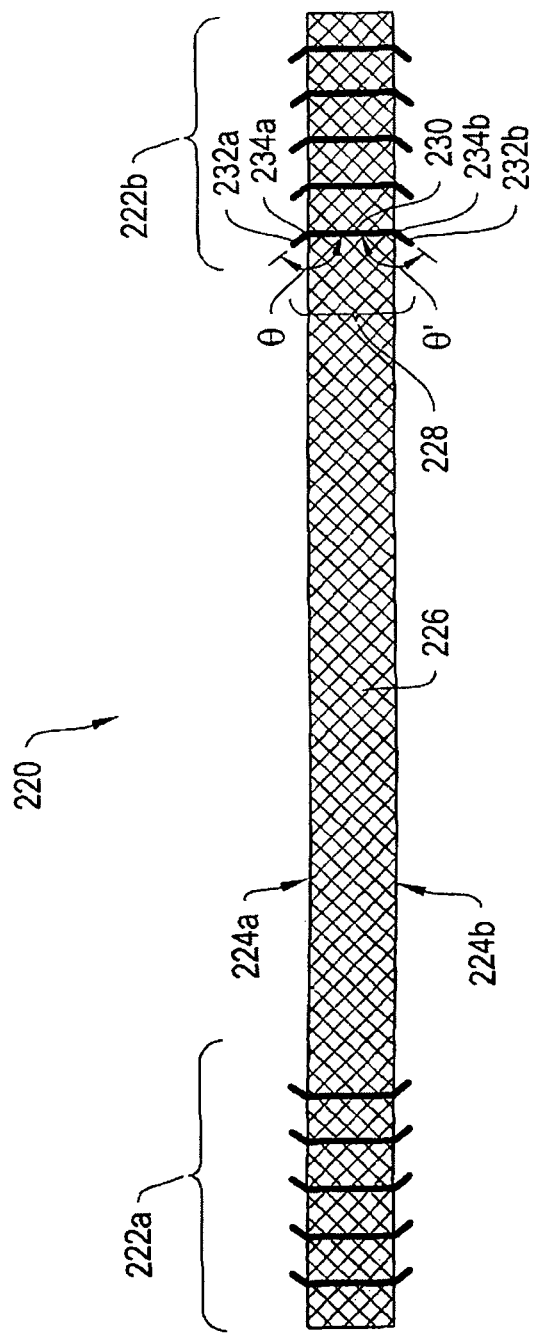

FIGS. 5 and 6 depict exemplary meshes incorporating bent stiffening members 208 and 228, respectively, that lie in the plane of the mesh 100 depicted in FIG. 1, protrude from the longitudinal edges 108a and 108b, and are disposed uniformly within the end regions 104a and 104b of the mesh 100. Each stiffening member 208 and 228 is secured to the mesh material at several points along the length of the stiffening member to help impede stretching of the mesh 100.

More particularly, FIG. 5 depicts an exemplary mesh 200 incorporating bent stiffening members 208 that are disposed generally transverse and oblique to the longitudinal axis of the mesh 200. Each stiffening member 208 has a long portion 210 with a portion 212 protruding from a longitudinal edge 204b of the mesh 200, and a short portion 214 joined to the long portion 210 to form a joint (or bend) 216, with the short portion 214 protruding from an opposing longitudinal edge 204a of the mesh 200. The bend 216 forms an angle ⊖ between portions 210 and 214, which is about 100° in FIG. 5. In certain embodiments the angle of the bend 216 is greater than 90°, while in certain embodiments the angle ⊖ is between about 90° and about 150°. In other embodiments the angle ⊖ is less than about 90°. In certain embodiments the angle is about 45° or less.

As shown, the bend 216 allows the edge protrusions 212 and 214 to extend from longitudinal edges 204a and 204b of the mesh 200 at acute angles to anchor end regions 202a and 202b of the mesh 200 into the tissue. In particular, the bent stiffening members 208 are oriented such that the longitudinal edge protrusions 212 and 214 are angled towards a center region 206, forming hooks along longitudinal edges 204a and 204b that are oriented to provide retrograde force in opposition to forces that arise during use and pull the end regions 202a and 202b towards the center region 206. The stiffening members 208 may also be disposed at varying distances along the mesh 100 depicted in FIG. 1 in configurations in which they overlap or form any other suitable arrangements and orientations.

FIG. 6 depicts an exemplary mesh 220 incorporating stiffening members 228 that have long portions 230 disposed generally transverse to the longitudinal axis of the mesh 220. Each stiffening member 228 also has longitudinal edge protrusions 232a and 232b joined to the long portions 230 to form bends 234a and 234b. The bends 234a and 234b form angles ⊖ and ⊖', respectively, between the long portion 230 and respective edge protrusions 232a and 232b. The protrusions 232a and 232b are adapted to penetrate the patient's tissue. In particular, and similar to the structure depicted in FIG. 5, the bends 234a and 234b allow the longitudinal edge protrusions 232a and 232b to extend from longitudinal edges 224a and 224b of the mesh 220 at acute angles which hook end regions 222a and 222b of the mesh 220 into the tissue. In particular, the bent stiffening members 228 are oriented such that the longitudinal edge protrusions 232a and 232b are angled towards a center region 226, forming hooks along longitudinal edges 224a and 224b that are oriented to provide retrograde force in opposition to forces that arise during use and pull the end regions 222a and 222b towards the center region 226. Similar to the straight stiffening members 128 of the mesh 120 depicted in FIG. 2, long portions 230 of the stiffening members 228 are substantially perpendicular to the longitudinal edges 224a and 224b of the mesh 220 to help prevent significant longitudinal stretching of the mesh 220. The stiffening members 228 may also be disposed at varying distances along the mesh 100 depicted in FIG. 1, in configurations in which they overlap or form any other suitable arrangements and orientations.

Figure 7:
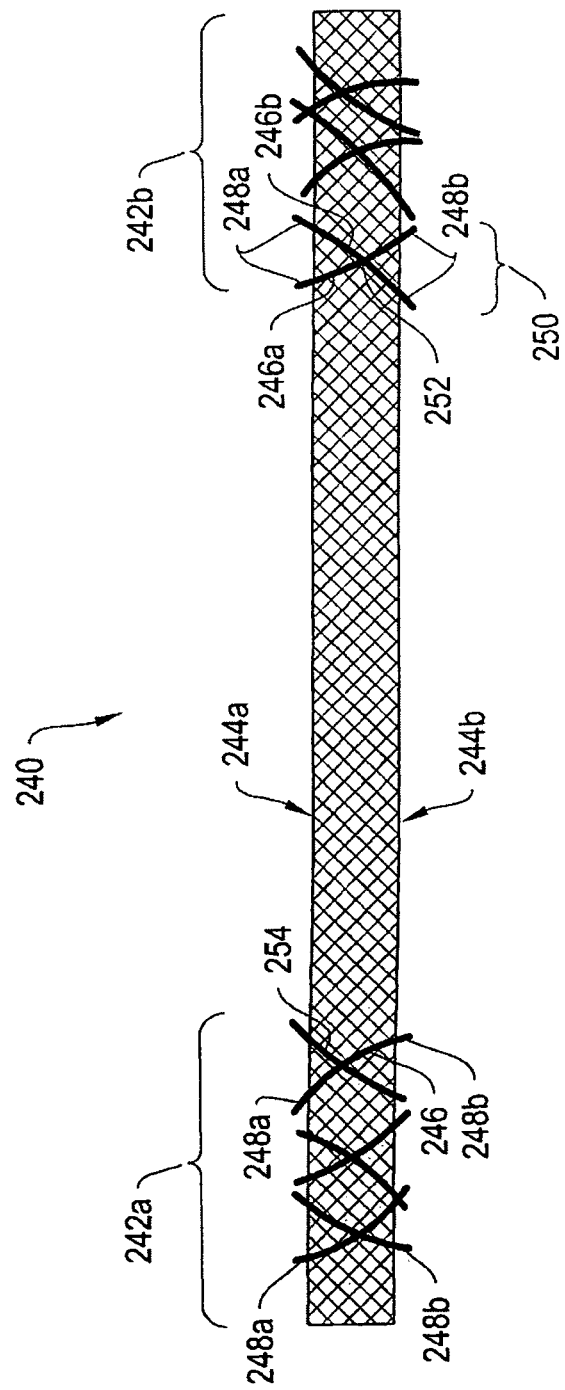
FIGS. 7 and 8 depict various exemplary meshes incorporating stiffening members with the sling of FIGS. 1A and 1B.
Figure 8:
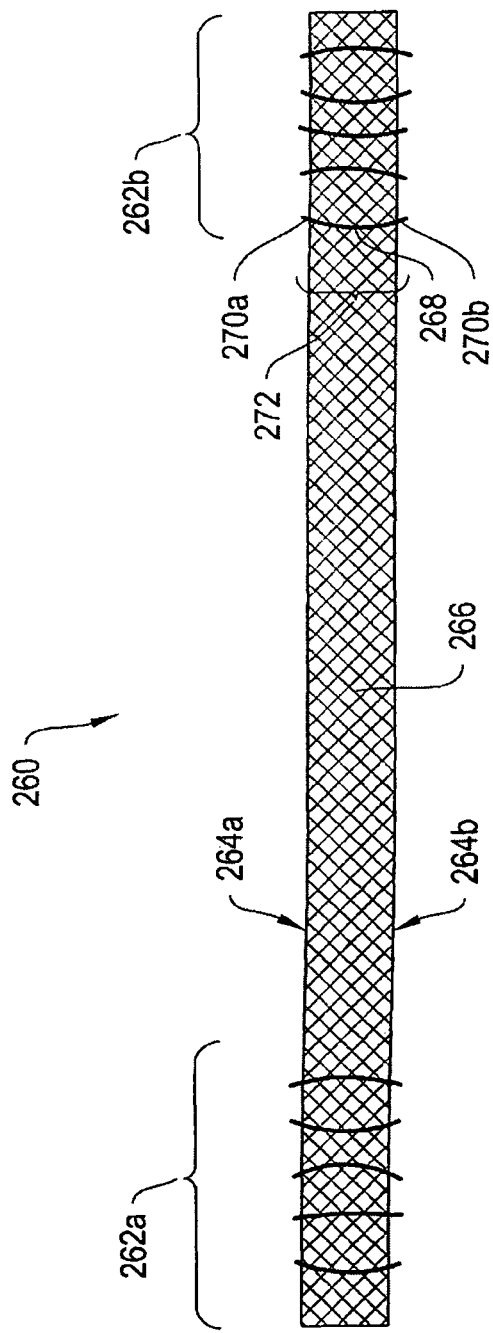

FIGS. 7 and 8 depict exemplary meshes incorporating curved stiffening members 246 and 268 disposed in the mesh 100 depicted in FIG. 1. As shown, the members 246 and 268 protrude from the longitudinal edges 108a and 108b and are disposed in the end regions 104a and 104b of the mesh 100. Each stiffening member 246 and 268 is secured to the mesh material at several points along the length of the stiffening member to help prevent significant stretching of the mesh 100. In certain implementations the members are disposed within the mesh by weaving through the holes 105. The members may also be glued, riveted, heat-melted or otherwise attached.

FIG. 7 depicts an exemplary mesh 240 incorporating curved stiffening members 246 arrayed in overlapping X structures 250. Similar to the X structures 170 depicted in FIG. 4, each X structure 250 has a "left" curved stiffening member 246a and a "right" curved stiffening member 246b which cross (and may optionally be secured together) at a crossing point 252 that lies substantially near the center of each curved stiffening member 246a and 246b. In other words, both stiffening members 246a and 246b in an X structure 250 are disposed generally transverse and oblique to the longitudinal axis of the mesh 240. In addition, each stiffening member in the X structure 250 forms a different angle with the longitudinal axis. By orienting each pair of curved stiffening members 246 in at least two directions, one direction generally parallel to the left curved stiffening member 246a and another direction generally parallel to the right curved stiffening member 246b, the mesh 240 is enhanced to impede stretching and thus render the mesh 240 more suitable for providing retropubic support in some patients. This feature may be enhanced by securing each curved stiffening member 246 to the mesh material at one or more points along the length of the mesh 240.

As shown, the curved stiffening member 246 has a slight curvature 254 and protrusions 248a and 248b adapted to penetrate the patient's tissue. The curvature 254 allows the protrusions 248a and 248b to extend from longitudinal edges 244a and 244b of the mesh 240 at acute angles not necessarily coplanar with the mesh 240. Because the orientation of the curvature 254 of each curved stiffening member 246 may vary within the mesh 240, the angles at which the protrusions 248a and 248b extend from the mesh 240 also vary, allowing end regions 242a and 242b of the mesh 240 to anchor to a non-uniformly shaped surface of the patient's tissue.

FIG. 8 depicts an exemplary mesh 260 incorporating curved stiffening members 268 arrayed approximately parallel to one another and transverse to the longitudinal axis of the mesh 260. Similarly to the straight stiffening members 128 of the mesh 120 depicted in FIG. 2, the curved stiffening members 268 are substantially perpendicular to the longitudinal axis of the mesh 260 to help prevent significant stretching of the mesh 260. Similarly to the curved stiffening member 246 in FIG. 7, the curved stiffening member 268 has a slight curvature 272 and protrusions 270a and 270b adapted to penetrate the patient's tissue. The curvature 272 allows the protrusions 270a and 270b to extend from longitudinal edges 264a and 264b of the mesh 260 at acute angles not necessarily coplanar with the mesh 260. Because the orientation of the curvature 272 of each curved stiffening member 268 may vary within the mesh 260, the angle at which the protrusions 270a and 270b extend from the mesh 260 may also vary, allowing end regions 262a and 262b of the mesh 260 to anchor to a non-uniformly shaped surface of the patient's tissue. The curved stiffening members 268 may also be disposed in the mesh 260 such that the curvature 272 of each curved stiffening member 268 is oriented as desired. For example, the curved stiffening members 268 could be oriented such that the protrusions 270a and 270b curve toward a center region 266 of the mesh 260, forming hooks along longitudinal edges 264a and 264b that are oriented to provide a retrograde force in opposition to forces that arise during use and pull the end regions 262a and 262b towards the center region 266. This may help provide a more secure fit for some patients.

FIGS. 9A and 9B depict, respectively, a top view and a side view of an exemplary mesh 280 incorporating curved stiffening members 286 that lie substantially in the plane of the mesh 280. As shown, members 286 protrude somewhat from top and bottom surfaces 284a and 284b of the mesh 280 and are disposed in end regions 282a and 282b thereof. Each stiffening member 286 may be secured to the mesh 280 at one or more points along the length of the stiffening member 286. The orientation of the curvature 290 of each curved stiffening member 286 alternates along the length of the mesh 280 (i.e., some members 286 are concave up and some are concave down), providing a substantially uniform arrangement of protrusions 288a and 288b from both the top and bottom surfaces 284a and 284b for securing the end regions 282a and 282b to the patient's tissue. The curved stiffening members 286 are aligned parallel to longitudinal edges 292a and 292b of the mesh 280, which helps prevent significant longitudinal stretching of the mesh 280. In certain implementations, the longitudinal stretching can be further impeded by attaching one or more of stiffening members 286 to the mesh 280 at several points along the length of the stiffening member 286, as noted earlier. While protrusions 288a and 288b may be maintained along the top and bottom surfaces 284a and 284b, the curved stiffening members 286 may also be disposed at varying distances along the mesh 280, in configurations in which they overlap, and in any other suitable arrangements and orientations.

FIGS. 10A-14B depict embodiments of exemplary meshes incorporating various fibrous members. The fibrous members may include strengthening knots and/or fibers in various thicknesses and combinations. As described in the illustrative exemplary embodiments, the strengthening knots and fibers may lie adjacent or interlaced with the holes 105 of the mesh 100 depicted in FIG. 1 to reinforce the mesh material. The knots and fibers may also be disposed uniformly or non-uniformly in the end regions 104a and 104b and, optionally, protrude from the top and bottom surfaces 106a and 106b to help improve mesh resilience, hold the mesh in place, and/or stimulate scar tissue ingrowth. Suitable materials and methods for manufacturing fibrous members and attaching them to the mesh 100 are described below.

FIGS. 10A and 10B depict top and side views of an exemplary mesh 300 incorporating strengthening knots 306 that are disposed non-uniformly throughout end regions 302a and 302b of the mesh 300, creating an irregular surface along both top and/or bottom surfaces 304a and 304b of the mesh 300. For example, a knot may be formed by tying a fiber around strands of the mesh 300 between two adjacent holes in the mesh 300. Knots 306 may also be formed by hot polymer that is dripped or otherwise applied to the mesh and then allowed to cool. The strengthening knots 306 may encourage scar tissue ingrowth and reinforce the material of the mesh 300. The strengthening knots may vary in size, with larger knots protruding more and potentially providing more strength than small knots, but also requiring more material to produce.

Figure 11:
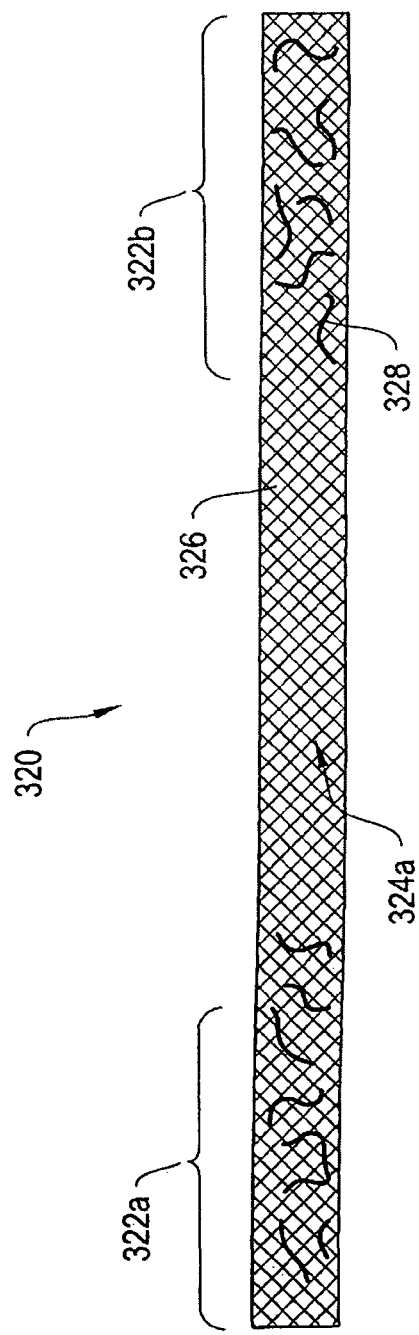
FIG. 11 depicts an exemplary mesh incorporating strengthening fibers with the sling of FIGS. 1A and 1B.

FIG. 11 depicts an exemplary mesh 320 incorporating strengthening fibers 328 disposed in various orientations and non-uniformly throughout end regions 322a and 322b of the mesh 320. Each of the depicted strengthening fibers 328 are interlaced within the holes 326 of the mesh 320 and secured to the mesh 320 at several points along the length of the fibers, which helps reinforce the resiliency of the mesh material and counteract stretching by the material. Portions of each strengthening fiber 328 may be configured to protrude from top and/or bottom surfaces 324a and 324b (not shown) to create an uneven surface along those surfaces, which may encourage scar tissue ingrowth. Strengthening fibers 328 may vary in thickness and length, with thicker strengthening fibers generally protruding more and longer strengthening fibers generally providing more resilience.

Figure 12:
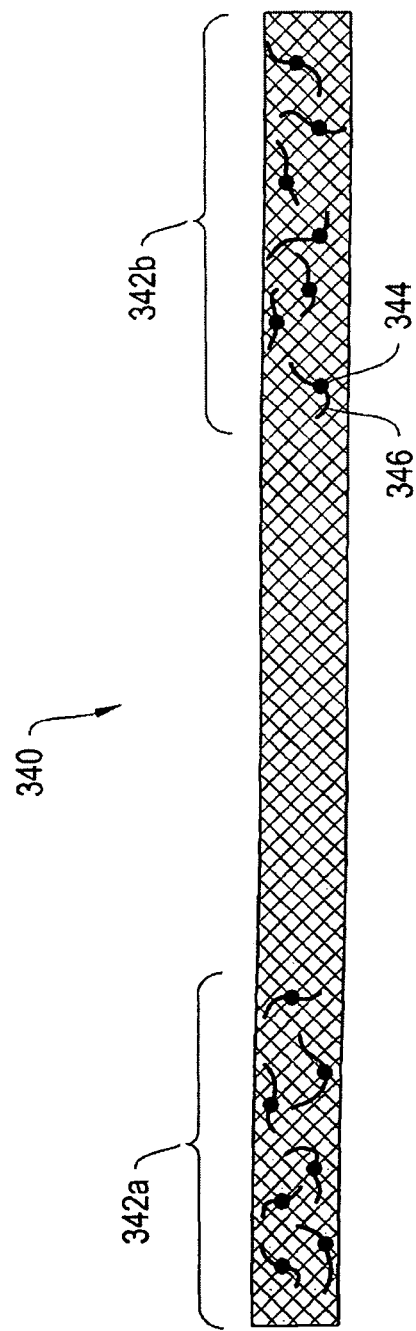
FIG. 12 depicts an exemplary mesh incorporating strengthening knots and fibers with the sling of FIGS. 1A and 1B.

FIG. 12 depicts an exemplary mesh 340 incorporating a combination of strengthening knots 344 and fibers 346 disposed in end regions 342a and 342b of the mesh 340. In certain embodiments, the strengthening knots 344 and fibers 346 are manufactured from the same material (e.g., polypropylene). In other implementations, the knots are formed of different material than the fibers.

The configuration of the strengthening components may be selected to achieve a desired mesh fit. For example, the strengthening knots 344 may be configured to protrude from a surface of the mesh 340 more than the strengthening fibers 346, which may allow the knots 344 to interact with the patient's tissue for anchoring to the tissue and/or stimulating scar tissue ingrowth. In other embodiments, the strengthening fibers 346 are configured to attach to more mesh surface area than do the strengthening knots 344, which may better strengthen the mesh material and resist stretching in some patients.

Figure 13:
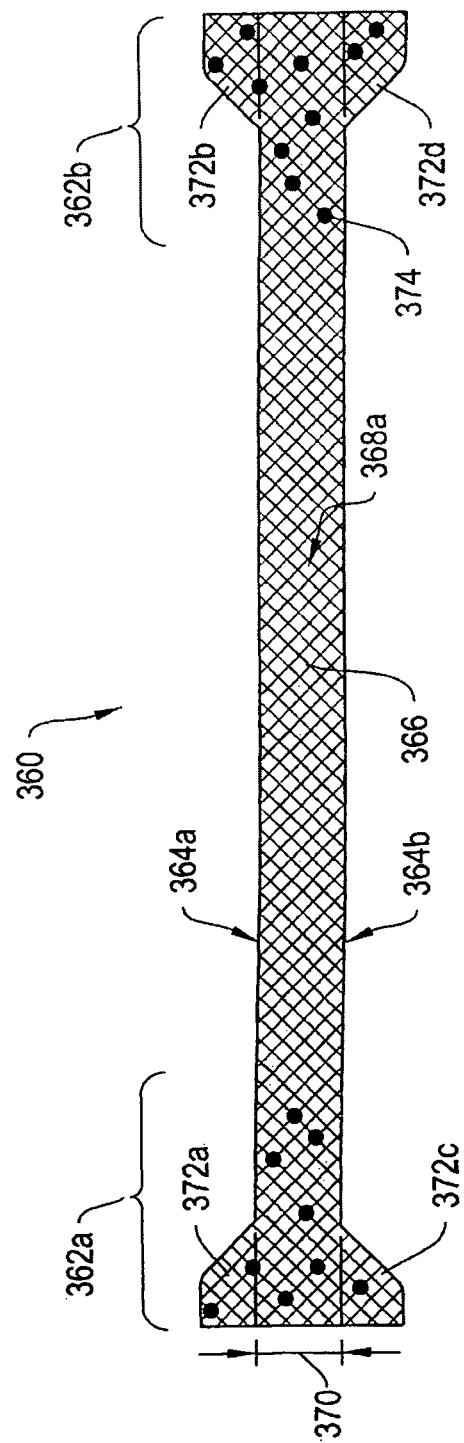
FIGS. 13, 14A, and 14B depict various exemplary mesh shapes incorporating resilient strengthening members.
Figure 14A:
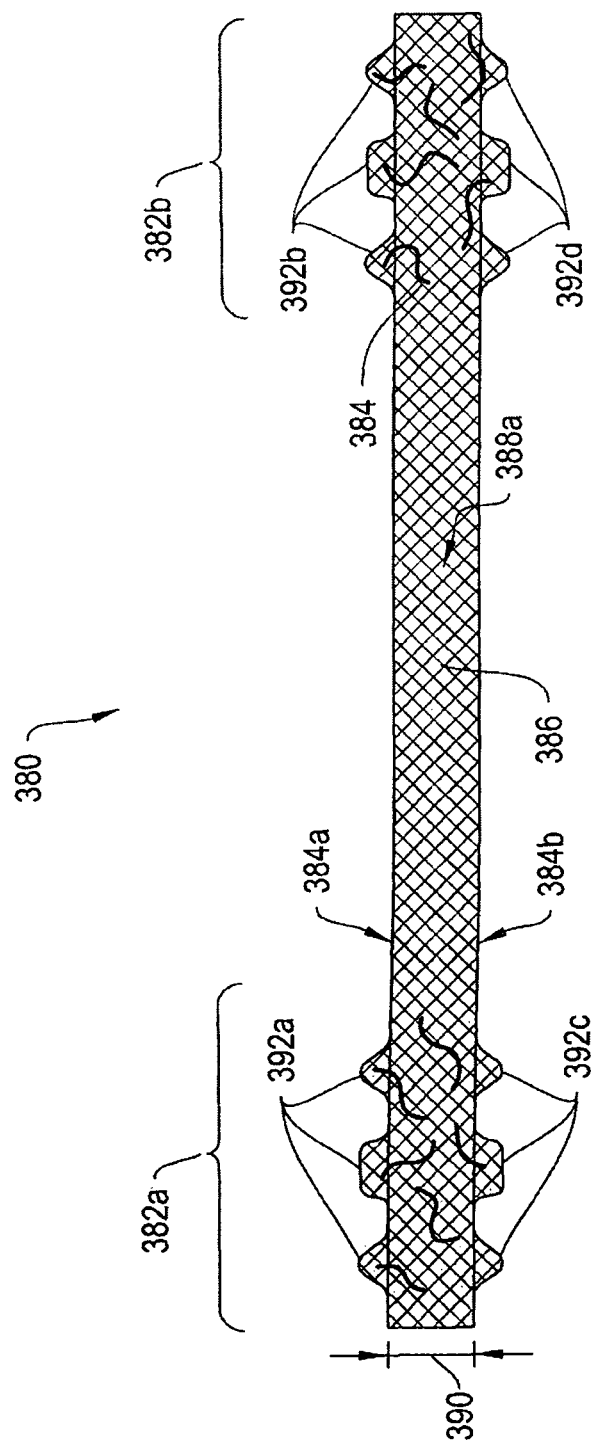
Figure 14B:
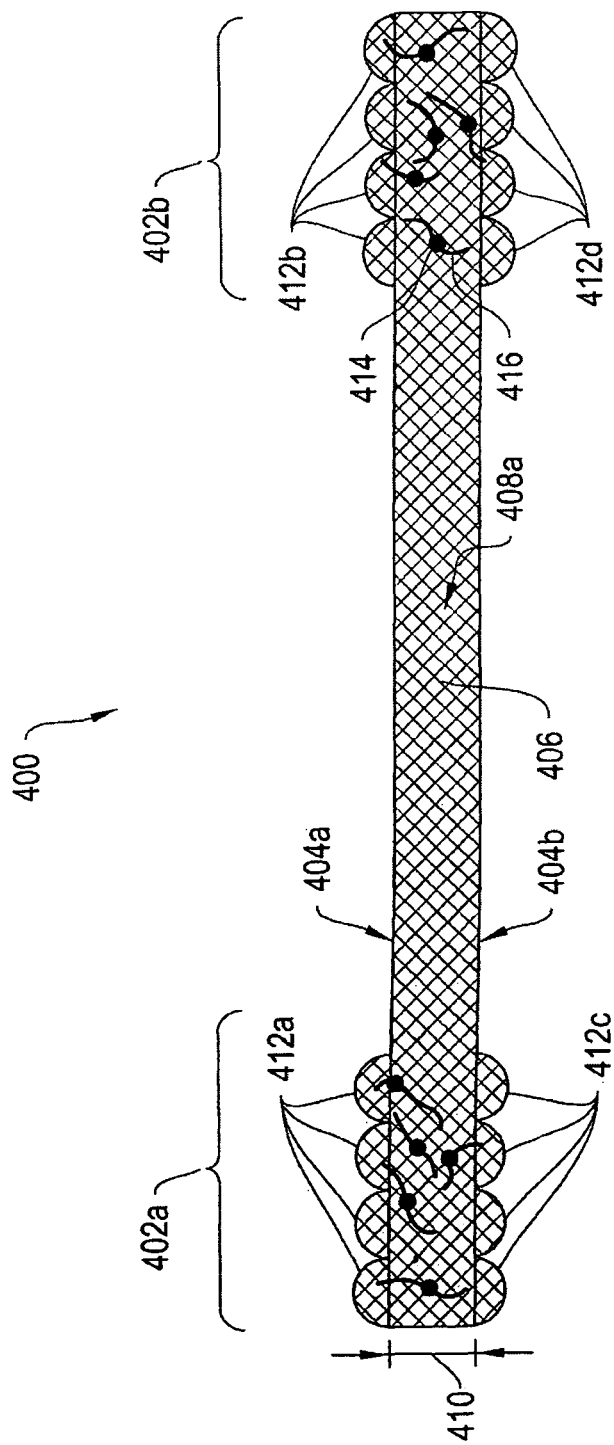

FIGS. 13, 14A, and 14B depict exemplary meshes 360, 380, and 400, respectively, featuring various mesh shapes and incorporating exemplary resilient strengthening members. The various mesh shapes, relative to the mesh 100 depicted in FIG. 1, have extended surface areas at end regions 104a and 104b, increasing the amount of surface area available for scar tissue in-growth and enhancing the ability of the end regions 104a and 104b to secure to the patient's tissues.

FIG. 13 depicts an exemplary mesh 360 with extended portions 372a and 372c of the mesh material at end region 362a and extended portions 372b and 372d of the mesh material at end region 362b. The extended portions 372a, 372b, 372c, and 372d are each configured as a trapezoidal tab, with portions 372a and 372b disposed lateral to a longitudinal edge 364a and portions 372c and 372d disposed lateral to a longitudinal edge 364b. The extended portions 372a, 372b, 372c, and 372d can fold inwardly to maintain a width 370 of the mesh 360 to reduce the delivery profile of the implant. A delivery profile refers to the maximum cross-sectional area of a passageway through the patient's anatomy that is required for delivery of the implant. The delivery profile may be affected by one or more of a number of factors, including the diameter of the delivery needles, shafts, and/or dilators, implant width, and protective sleeve width. Reducing the delivery profile of the implant decreases the size of an incision through which the mesh 360 must travel during implantation. In certain embodiments, the delivery profile of the mesh is low, but the mesh is configured to expand (e.g., by the unfolding of one or more extended portions 372a-372d) upon implantation to provide added anchoring security. In certain embodiments, the extended portions 372a, 372b, 372c, and 372d may be disposed closer to or further from a center region 366 of the mesh 360, as desired for implantation in particular locations. To help improve mesh resiliency and strength, the mesh 360 may include one or more resilient strengthening members, such as strengthening knots 374, which are shown disposed in end regions 362a and 362b. The mesh 360 may also have one or more of any of the other strengthening members disclosed herein.

FIG. 14A depicts an exemplary mesh 380 with extended portions 392a and 392c of the mesh material at end region 382a and extended portions 392b and 392d of the mesh material at end region 382b. The extended portions 392a, 392b, 392c, and 392d each include a plurality of tabs, with portions 392a and 392b disposed lateral to the longitudinal edge 384a and portions 392c and 392d disposed lateral to longitudinal edge 384b. The extended portions 392a, 392b, 392c, and 392d can fold inwardly to maintain a width 390 of the mesh 380 to decrease the delivery profile of the mesh 380. The mesh 380 may have one or more tangs disposed along the longitudinal edges 384a and 384b to help stimulate scar tissue ingrowth and tissue adherence by the end regions 382a and 382b. In certain embodiments, the tangs anchor the mesh in soft tissue. The extended portions 392a, 392b, 392c, and 392d may be disposed closer or further from a center region 386 of the mesh 380 as desired for implantation in desired locations. To help improve mesh resiliency and strength, the mesh 380 may have various resilient strengthening members, such as strengthening fibers 394, which are shown disposed in end regions 382a and 382b. The mesh 380 may also have one or more of any of the other strengthening members disclosed herein.

FIG. 14B depicts an exemplary mesh 400 with extended portions 412a and 412c of the mesh material at end region 402a and extended portions 412b and 412d of the mesh material at end region 402b, similar to extended portions 392a-392d of FIG. 14A. The extended portions 412a, 412b, 412c, and 412d each include a plurality of rounded tabs, with portions 412a and 412b disposed lateral to longitudinal edge 404a and portions 412c and 412d disposed lateral to longitudinal edge 404b. The extended portions 412a, 412b, 412c, and 412d can fold inwardly to maintain a width 410 of the mesh 400 to decrease the delivery profile of the mesh 400. The mesh 400 may have one or more tangs disposed along the longitudinal edges 404a and 404b to help stimulate scar tissue ingrowth and tissue adherence by the end regions 402a and 402b. In certain embodiments, the tangs anchor the mesh in soft tissue. The extended portions 412a, 412b, 412c, and 412d may be disposed closer or further from a center region 406 of the mesh 400 as desired for implantation in desired locations. To help improve mesh resiliency and strength, the mesh 400 may have various resilient strengthening members, such as strengthening knots 414 and fibers 416, which are shown disposed in end regions 402a and 402b. The mesh 400 may also have one or more of any of the other strengthening members disclosed herein.

FIGS. 15A and 15B depict, respectively, a top view and a side view, of an exemplary aggressive mesh 420 incorporating a plurality of resilient strengthening members disposed on and within the mesh 420 and adapted to improve mesh resiliency and ability of the mesh 420 to adhere to the patient's tissue. As shown, the resilient strengthening members include retention nodules 428, strengthening bars 430, soft tissue anchors 432, and other members such as those described herein. Suitable materials and methods for manufacturing resilient strengthening members and attaching them to the mesh 100 are described below.

One or more of the retention nodules 428 has a conical point that protrudes from the top and bottom surfaces 424a and 424b of the nodule or nodules. The nodules 428 may be deposited on one or more exterior surfaces without necessarily penetrating through them, and each may attach at several points at which strands of the mesh 420 intersect or cross. The nodules 428 thus may strengthen the mesh material and create an irregular surface of pointed bumps conducive to scar tissue ingrowth. In one embodiment, the nodules 428 may be disposed on only one of the top and bottom surfaces 424a and 424b, for example only on the top surface 424a as shown. This embodiment may be advantageous for cases when there are regions of the mesh 420 where it is desirable that one surface interacts with the patient's tissue but the opposing surface does not.

The depicted strengthening bars 430 are rigid, have an oblong shape, and lie within the plane of the mesh 420 preferably parallel to longitudinal edges 426a and 426b. The bars 430 may be deposited on and penetrate through top and bottom surfaces 424a and 424b, and preferably each attach at several points to strands of the mesh. The bars 430 help improve the resiliency and stability of the mesh material by counteracting any tendency to stretch. The bars 430 may also be oriented generally transverse to the longitudinal axis of the mesh or according to any other suitable orientations and arrangements. The bars may be formed of plastic, metal, composites, or any other suitable stiffening material.

Anchors 432 are disposed coplanar to the mesh 420 at end regions 422a and 422b. The mesh 420 also has an optional anchor 432 disposed on one or more ends. The anchors 432 serve to anchor end regions 422a and 422b of the mesh 420 to anchoring locations within the patient's body. Various anchor implementations are described in U.S. patent application Ser. No. 11/152,898, entitled "Systems, Methods and Devices Relating to Implantable Supportive Slings," and/or in U.S. application Ser. No. 11/400,111, entitled "Systems, Devices and Methods for Treating Pelvic Floor Disorders," filed Apr. 6, 2006, the contents of which are hereby incorporated by reference in their entirety, each of which is herein incorporated by reference in its entirety.

Other exemplary soft tissue anchors that may be used with the meshes described herein are depicted in FIGS. 16A-17A. In FIG. 16A, the anchor 440 includes a through-aperture 442, a body 444 and two rows of radial projections, or barbs 446. The through-aperture 442 couples to a shaft of a delivery device by fitting around the shaft, as will be discussed below. The depicted through-aperture 442 extends axially entirely through the body 444 of the anchor 440. In other embodiments, the body 444 includes a passage extending axially from the proximal end 440b of the anchor 440 only part way to the distal end 440a of the anchor 440.

The barbs 446 are relatively short (e.g., less than about 2 millimeters in length) and relatively wide (e.g., between about 1 millimeter and about 2 millimeters in width/diameter). Additionally, they have relatively flat terminal ends 448. The barbs 446 are also flexible. When an operator inserts the anchor 440 into an obturator membrane, the barbs 446 flex and compress against the body 444 of the anchor 440 to allow passage at least partially through the obturator membrane. After insertion within the obturator membrane, the barbs 446 expand radially from the body 444 and thereby resist retrograde motion back through the obturator membrane, thereby impeding the anchor 440 from disengaging from the obturator membrane.

FIG. 16B shows an alternative embodiment of an anchor 450, having a through-aperture 452, a body 454 and two rows of radial projections 456. The projections 456 are relatively long (e.g., greater than or equal to about 2 millimeters in length) and relatively wide (e.g., between about 1 millimeter and about 2 millimeters in width/diameter), as compared with anchor 440 of FIG. 16A.

FIG. 16C shows another embodiment of an anchor 460 having a body 462, an axially extending through-aperture 464 and radial projections 466. The anchor 460 is similar to anchors 440 and 450 of FIGS. 16A and 16B, respectively, except that the radial projections 466 have pointed rather than flat terminal ends, in contrast to the projections 446 and 456. The pointed projections 466 impede retrograde forces that may be applied to the anchor 460, since the projections 466 more firmly incise into and engage with the tissue of the obturator membrane and thereby prevent disengagement of the anchor 460 from the obturator membrane. In particular, the projections have an initial width at a base 468 comparable to the width of the projections 446 and 456, and have a length similar to that of the projections 446.

FIG. 16D shows another illustrative anchor 480, including a relatively long (e.g., between about 2.5 centimeters and about 3.5 centimeters) body 482 and five rows of relatively long (e.g., greater than about 5 millimeters) radial projections 484. As in the case of the above described examples, the anchor 480 includes a radially extending through-passage 486.

Figure 16E:
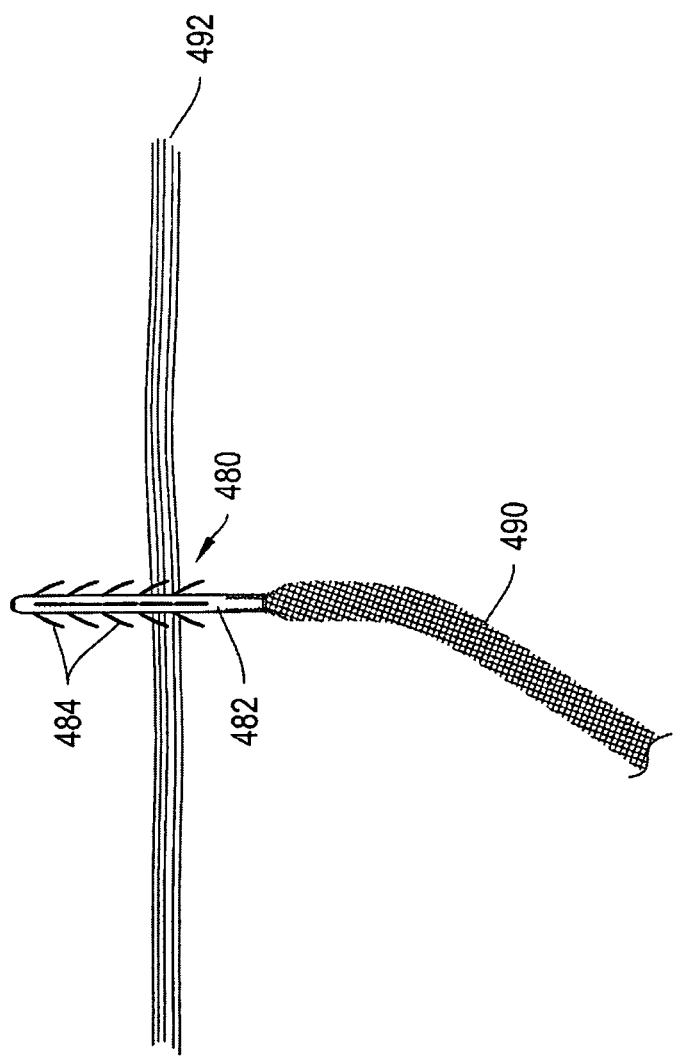

FIG. 16E shows the barbed anchor 480 coupled to a portion of a surgical implant 490 and anchored to an obturator membrane 492. In operation, an operator drives the anchor 480 partially (as illustrated) or entirely through the obturator membrane 492 using a delivery device and/or method that will be discussed below. The barbs 484 on the anchor 480 engage with the obturator membrane 492 and inhibit the anchor 480 from retracting out of the membrane 492 after insertion. An operator then optionally drives the anchor 480 further into the obturator membrane 492 to tension the associated surgical implant 490. The long body 482 is beneficial in part because the operator can drive the anchor 480 various distances through the obturator membrane 492, corresponding to various tensions of implant 490. When the operator drives the anchor 480 entirely through the obturator membrane 492, the surgical implant 490 is driven through the obturator membrane 492. The implant 490 may have tangs and/or resilient strengthening members to engage with and anchor to the obturator membrane 492. The operator can then extend or retract a portion of the implant 490 through the obturator membrane 492 to tension the implant 490.

Figure 17A:
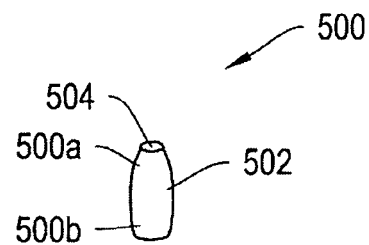
FIGS. 17A-17C depict exemplary soft tissue anchors and techniques for implantation in a patient's tissue.
Figure 17B:
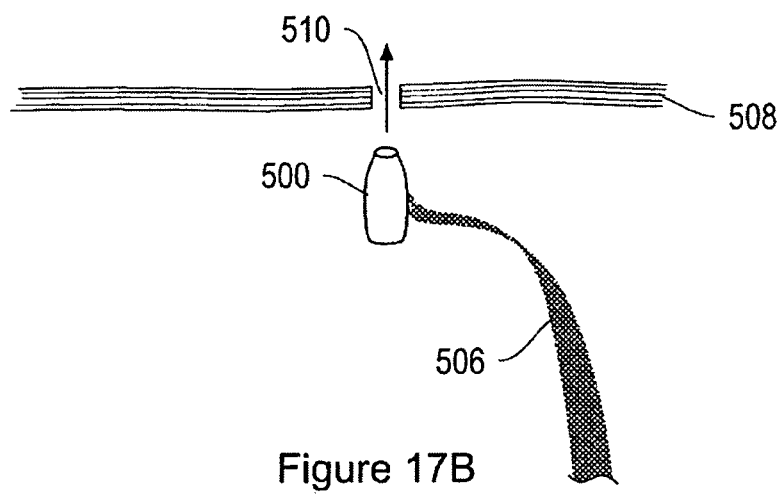
Figure 17C:
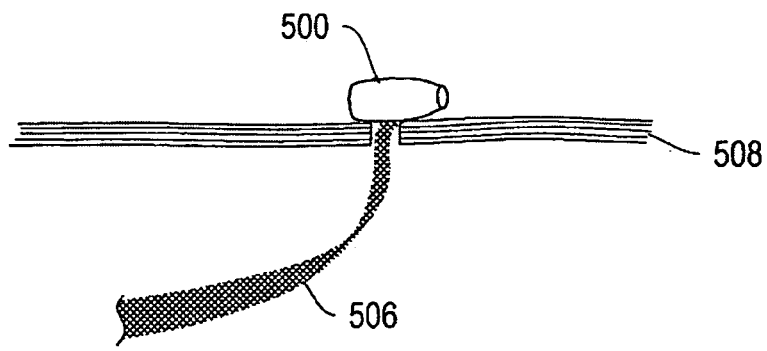

FIGS. 17A-17C depict an exemplary barbless soft tissue anchor and a corresponding technique for using the anchor. FIG. 17A illustrates a soft tissue anchor 500 having a smooth outer surface 502. Like the anchors depicted in FIGS. 16A-16E, the anchor 500 includes a through-aperture 504 that fits around the shaft of a delivery device, as will be discussed below. The depicted through-aperture 504 extends axially entirely through the anchor 500. In other embodiments, the anchor 500 includes a passage extending axially from the proximal end 500b of the anchor 500 only part way to the distal end 500a of the anchor 500.

FIGS. 17B and 17C illustrate an exemplary technique for using the anchor 500 to anchor a surgical implant 506 to an obturator membrane 508. In particular, an operator forms an aperture 510 within the obturator membrane 508 using, for example, a needle or dilator. Next, the operator couples the anchor 500 to an implant 506 using methods discussed below. The operator then drives the anchor 500 through the aperture 510. When retrograde tension is applied to the implant 506, the anchor 500 pivots to a horizontal orientation, depicted in FIG. 17C, and aligns with the obturator membrane 508, and this horizontal orientation prevents the anchor 500 from disengaging from the obturator membrane 508.

Figure 18:
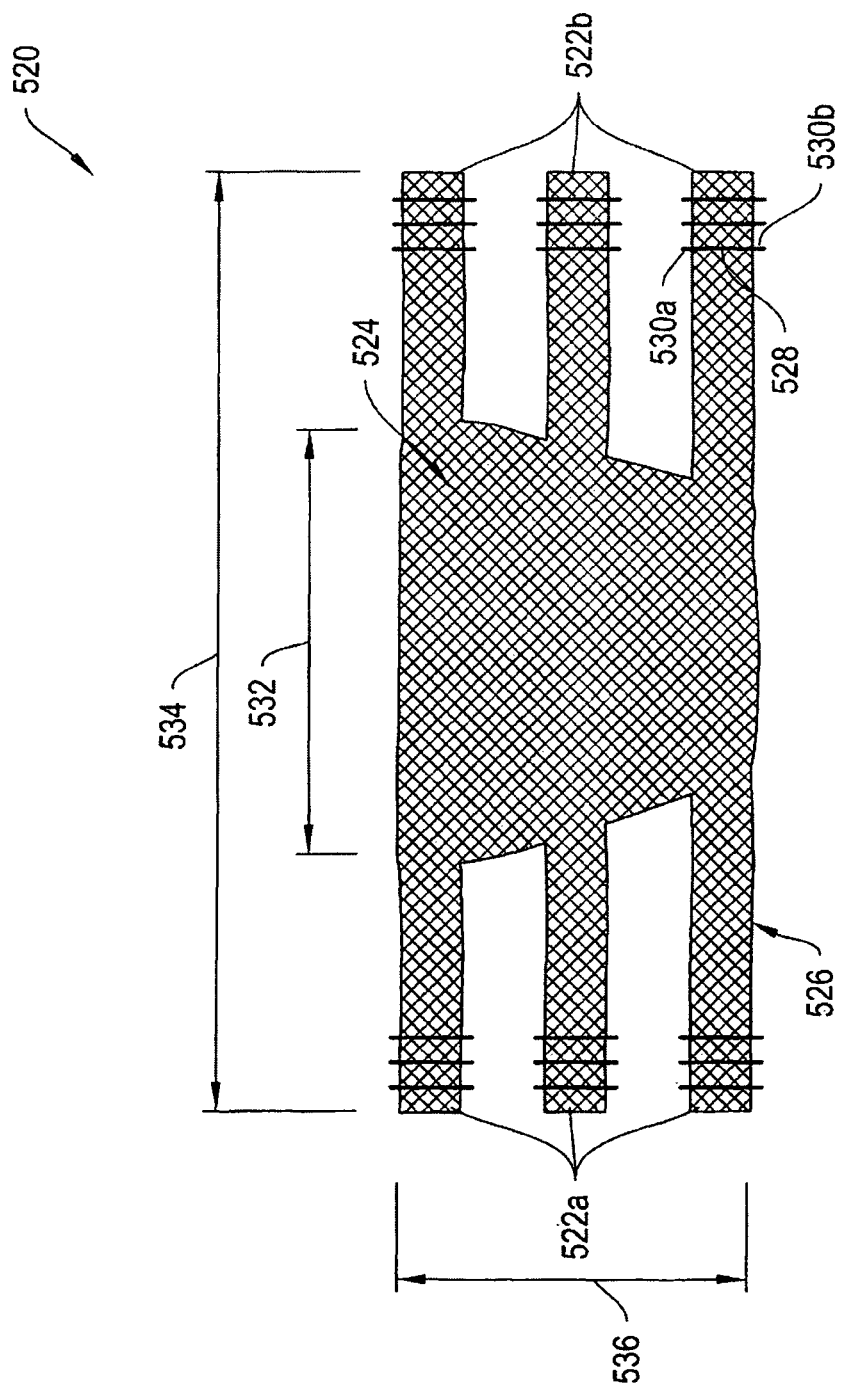
FIGS. 18 and 19 depict various exemplary pelvic floor meshes incorporating strengthening members.
Figure 19:
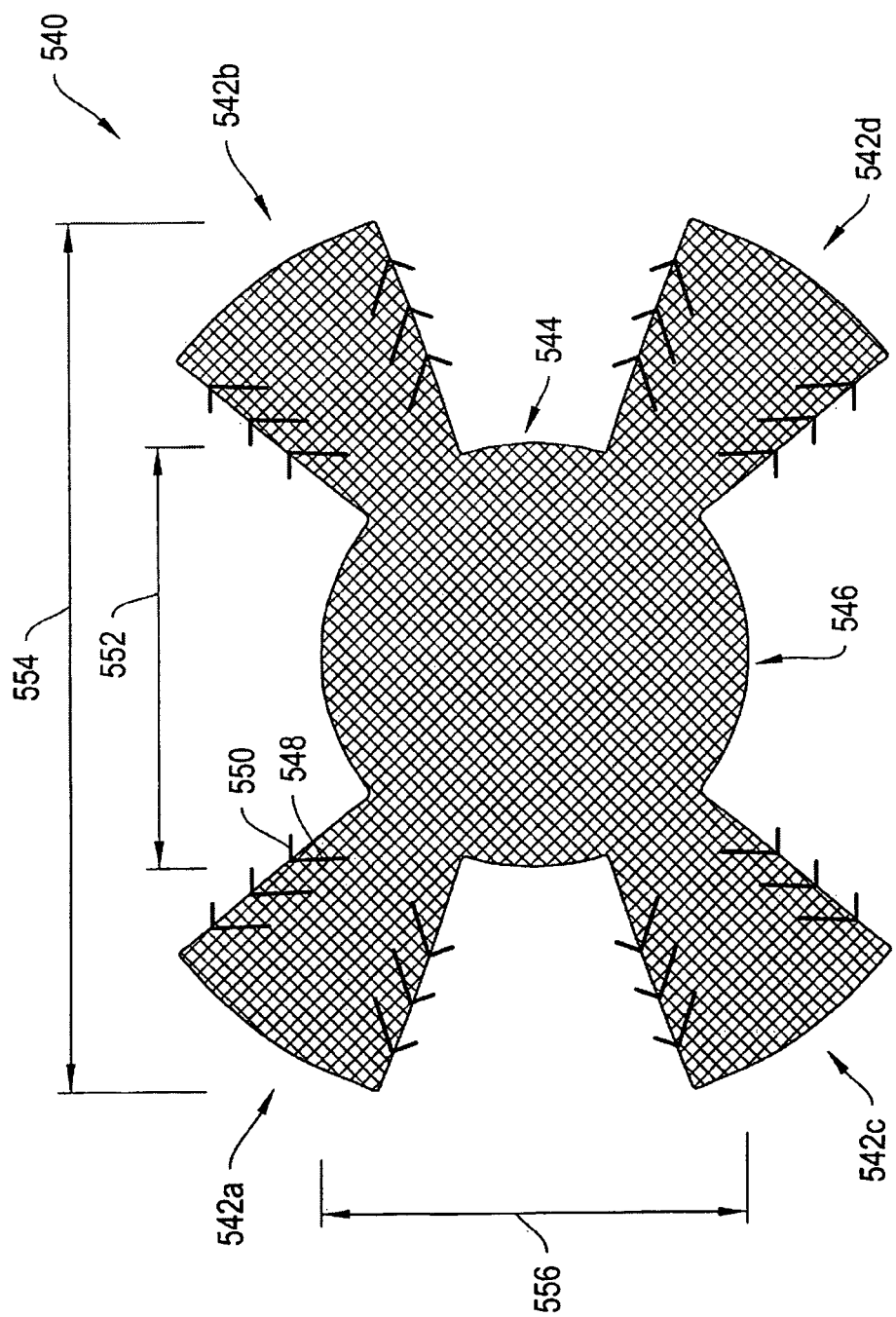

FIGS. 18 and 19 depict exemplary meshes 520 and 540, respectively, sized and shaped for prolapsed organ support. Relative to the mesh 100 depicted in FIG. 1, the pelvic floor meshes 520 and 540 are wider and may have more end regions for securing the mesh within the patient. The mesh material of pelvic floor meshes 520 and 540 have a network of spaced holes 1605 and 1705, respectively, that serve as a lattice upon which scar tissue may grow. The mesh shape and arrangement of end regions may be selected as desired, depending on the shape and location of the prolapsed organ. The pelvic floor meshes 520 and 540 may feature resilient strengthening members (e.g., any of the nodules, fibers, or other strengthening member disclosed herein) to help strengthen the mesh material, prevent significant stretching of the mesh material, and secure the mesh to the patient's tissue, as described herein.

Pelvic floor mesh 520, depicted in FIG. 18, has a trapezoidal center region 524 surrounded by two opposing sets 522a and 522b of three end regions each, where each end region is adapted to be implanted in a patient's tissue to hold the sling in the pelvic region of the patient. A perimeter 526 of the mesh 520 may have tangs, which are ends of fibers of the mesh material, that project from the perimeter 526 of the mesh 520 and are adapted to penetrate patient tissue. The tangs may interact with the patient's tissue by hooking into and adhering to the patient's tissue or stimulating scar tissue ingrowth. The mesh 520 may also or alternatively incorporate resilient strengthening members such as those described herein. For example, the sets 522a and 522b of end regions may have straight stiffening members 528 lying in a plane of the mesh 520 and having perimeter protrusions 530a and 530b adapted to penetrate the patient's tissue to secure the sets 522a and 522b of end regions within the patient.

The mesh 540, depicted in FIG. 19, has four end regions 542a, 542b, 542c, and 542d equally spaced around a circular center region 544, where each end region is adapted to be implanted in a patient's tissue to hold the sling in the pelvic region of the patient. A portion of, or substantially all of, the perimeter 546 may have tangs. The mesh 540 may also incorporate resilient strengthening members, as described above. For example, the end regions 542a, 542b, 542c, and 542d may have stiffening members 548 that are bent and disposed in a plane of the mesh 540, and may also have perimeter protrusions 550 adapted to penetrate the patient's tissue to secure the end regions 542a, 542b, 542c, and 542d within the patient.

Either mesh 520 or 540 can have a length suitable for allowing the mesh to span the region of the patient's retropubic space between its two obturator membranes. In certain embodiments, the mesh has a center region length 532 or 552, respectively, of between about 5 cm and about 8 cm. Either mesh 520 or 540 can have an overall longitudinal length 534 or 554, respectively, such as greater than about 7 cm, greater than about 9 cm, or from between about 10 cm to about 15 cm, and thus be sized to span the patient's full obturator-to-obturator length and the anchor two or more of the end regions 542a-542d in respective obturator membranes.

Either mesh 520 or 540 can have an anterior-to-posterior width 536 or 556, respectively, of between about 2.5 centimeters and about 8 centimeters, which allows the mesh to extend under and provide hammock-like support to posterior regions of the pelvic region, including, for example, the base of the bladder. In general, the mesh can have any desired anterior-to-posterior lengths to support various anatomical regions of the pelvic floor. For example, either mesh 520 or 540 can have an anterior-to-posterior length 536 or 556, respectively, of greater than about 3 cm, greater than about 5 cm, greater than about 7 cm, or greater than about 10 cm to support the patient's urethra, bladderneck, and/or bladder.

Figure 20:
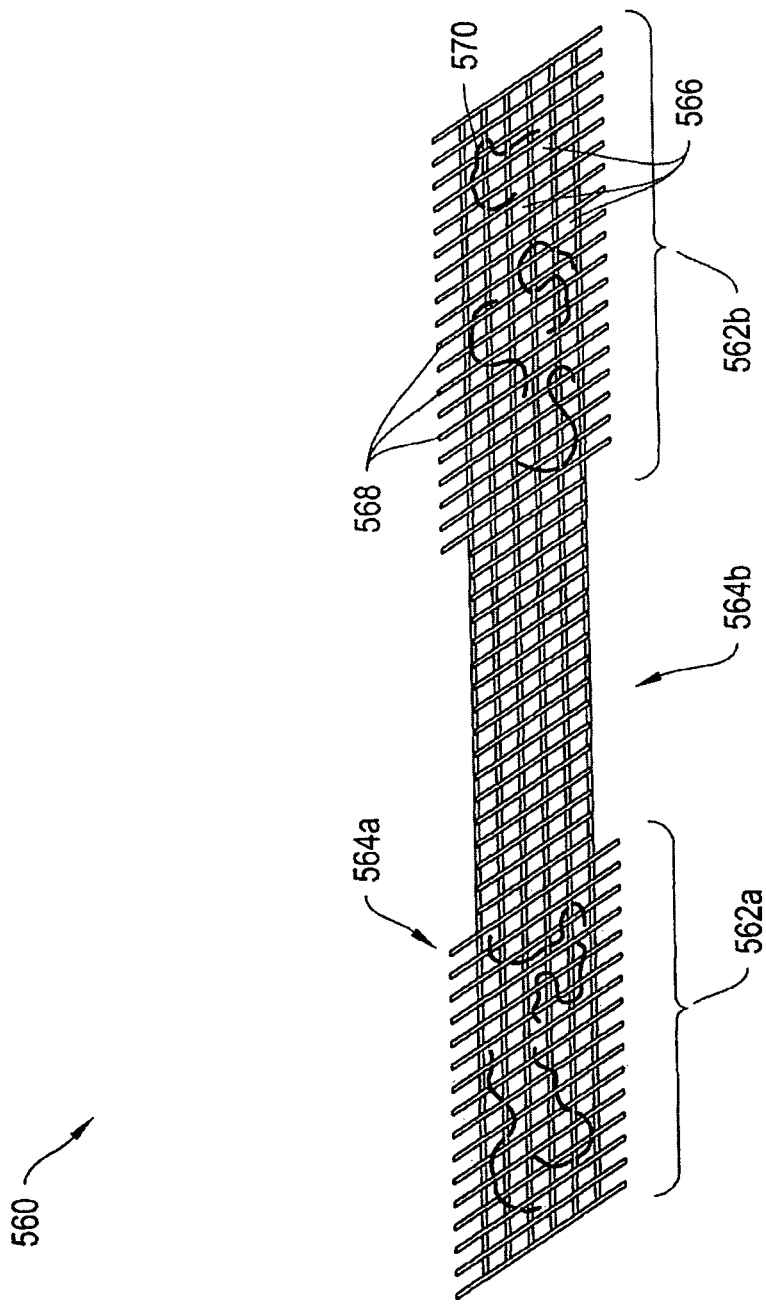
FIG. 20 depicts an exemplary tanged mesh incorporating strengthening members.

FIG. 20 depicts an exemplary mesh 560 incorporating resilient strengthening members. The mesh 560 has tangs 568 disposed along longitudinal edges 564a and 564b to help stimulate scar tissue ingrowth and tissue adherence by end regions 562a and 562b. In certain embodiments, the tangs anchor the mesh in soft tissue. To help improve mesh resiliency and strength, the mesh 560 may have various resilient strengthening members, such as strengthening fibers 570, which are shown interlaced with holes 566 of the mesh 560 and disposed in the end regions 562a and 562b. The mesh 560 may also have one or more of any of the other strengthening members disclosed herein.

The exemplars described above in reference to FIGS. 2-20 are viable alternatives for mesh enhancement and serve merely as examples of suitable meshes and suitable resilient strengthening members. A specific mesh can optimize the number, types, orientations, and arrangement of resilient strengthening members taking into consideration variables such as mesh shape, implantation procedure, implantation location, organ to be supported, and cost of materials and manufacturing. In certain embodiments the resilient strengthening members are disposed in end regions of the mesh, spaced away from a center region of the mesh. The center region can underlie and support a urethra, bladderneck, or prolapsed pelvic organ within the patient, and may be left free of protrusions to avoid damaging or irritating the supported pelvic structure. In certain embodiments, a resilient strengthening member is disposed about mid-way between an end edge of the mesh and its center. In certain embodiments, the member is disposed about 10% of the way from the edge to the center. In other embodiments the member is disposed closer to the center (e.g., between about mid-way to about 90% of the way to the center). Moreover, the concentration of strengthening members may vary according to the needs of the patient and depending on the types, sizes, and variety of strengthening members, the implantation locations, and the implantation procedure. About 10% to about 90% of the surface area of the mesh is coupled to a resilient strengthening member, and about 20% to about 40% of the mesh surface area is coupled to a strengthening member in certain implementations.

Exemplary methods and devices for delivering the exemplary meshes disclosed herein to an anatomical location within the patient are described below in reference to FIGS. 21-26B. Approaches that may be appropriate include transobturator, suprapubic, prepubic, and transvaginal approaches. Other approaches may also be appropriate. All operative combinations between the disclosed meshes, resilient strengthening members, delivery devices and these procedures are contemplated. Any of the delivery devices described above may be employed to create a passage through body tissue, for example, from the inferior pubic ramus through the obturator foramen to the vagina or the reverse according to the methodologies described herein.

Figure 21:
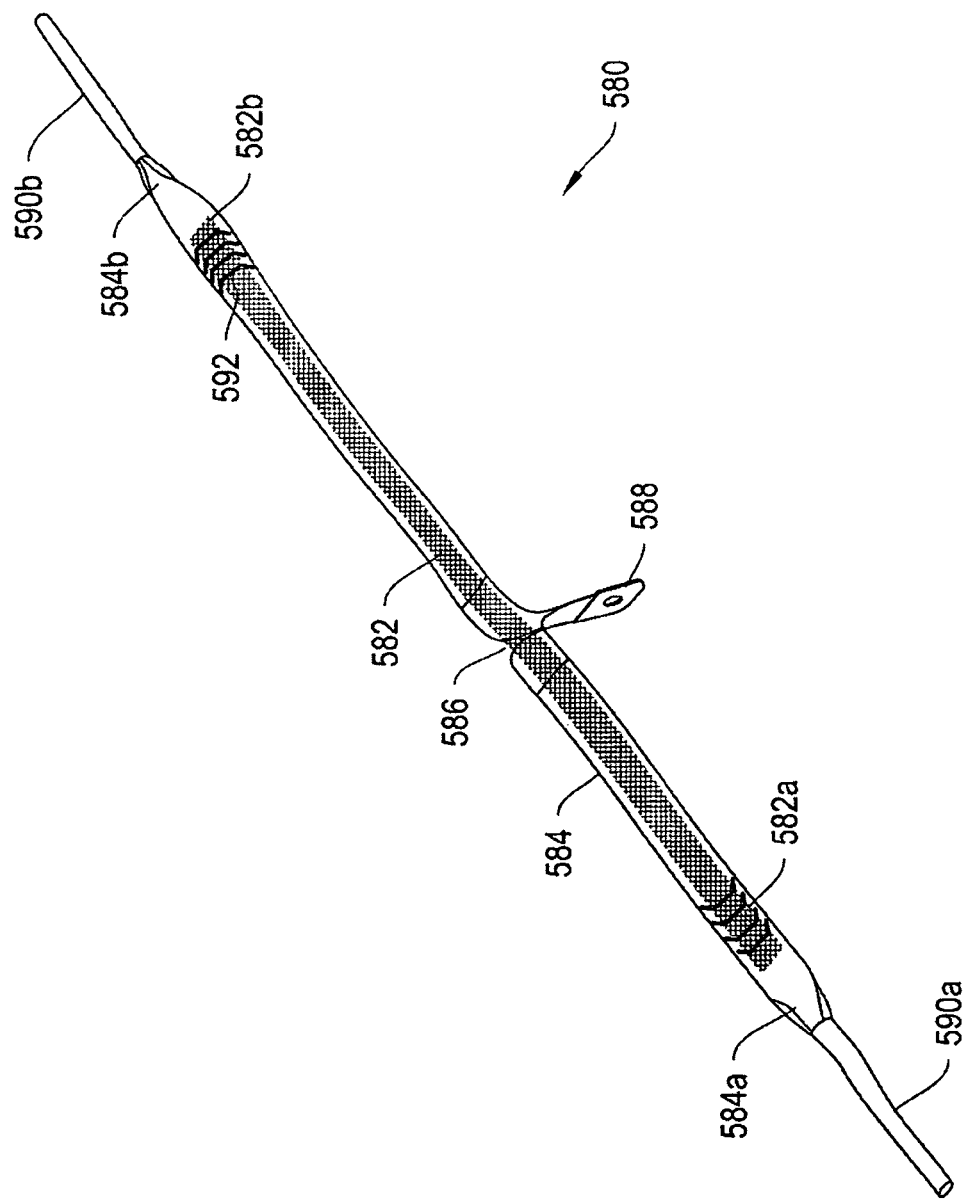
FIG. 21 depicts an exemplary sleeve for use in delivering an exemplary mesh.

As depicted in FIG. 21, in certain implementations an exemplary mesh 582 is positioned within a sleeve 584 to aid in delivery of the mesh 582. The mesh 582 can incorporate various resilient strengthening members, such as stiffening members 592 disposed in the end regions 582a and 582b of the mesh 582, similar to mesh 220 of FIG. 6. The mesh 582 may also have one or more of any of the other strengthening members disclosed herein. Each end of the sleeve 584 connects to a dilator tube 590a or 590b which is connected to a respective end portion 584a and 584b, of the sleeve 584. The dilator tubes 590a and/or 590b may taper in a direction toward or away from the midpoint of the sling assembly 580 depending on into which end of the guide tube a delivery device shaft is to be inserted. An exemplary delivery device is described below in reference to FIG. 22. The dilator tubes may be affixed to the sling assembly 580 ends by any suitable mechanism, including gluing, heat bonding, shrink tubing or the like.

In certain embodiments, the dilator tubes 590a and 590b are designed to slide onto the guide tube of a delivery device. In certain embodiments, the inner diameter of the dilator tubes 590a and 590b is larger than the diameter of the curved shaft or the diameter of at least one section of the shaft, e.g., the distal end of the shaft. The dilator tubes 590a and 590b may be constructed so that the tip of the shaft entrains the dilator tubes 590a and 590b and carries them with it when the shaft is extended from the guide tube. In the depicted embodiment, the dilator tubes 590a and 590b are bonded to the sleeve 584, such that the dilator tubes 590a and 590b secure the respective ends 584a and 584b of the sleeve 584 of the sling assembly 580 to the tip of the delivery device and facilitate expansion of tissue along a respective path during sling assembly placement. In other embodiments, the dilator tubes may include hooks or loops configured to engage in mating structures, such as L-slots, formed onto the tip of the shaft. As described below, in other embodiments, the tubes 590a and 590b are soft tissue anchors that are bonded to the sling and adapted to anchor the sling to the patient's tissues and remain in place after placement of the sling. In certain embodiments, the tubes 590a and 590b are made of a biodegradable material.

The sleeve 584 may be made, for example, from one or more absorbent materials, such as a sponge-like material, that can optionally be pre-soaked in a drug solution, for example, in an anesthetic, anti-inflammatory, coagulating, anticoagulating, or antibiotic solution. In another embodiment, the sleeve 584 may be made from a non-wettable material, such as polypropylene, polyethylene, polyester, polytetrafluoroethylene (available from DuPont Corporation, Wilmington, Del., under the trademark TEFLON™, TYVEK™, MYLAR™), or copolymers thereof. The non-wettable materials can also be pretreated with a therapeutically effective drug coating. The sleeve 584 is preferably transparent so that an operator will be able to see the mesh 582 inside the sleeve 584.

Figure 22:
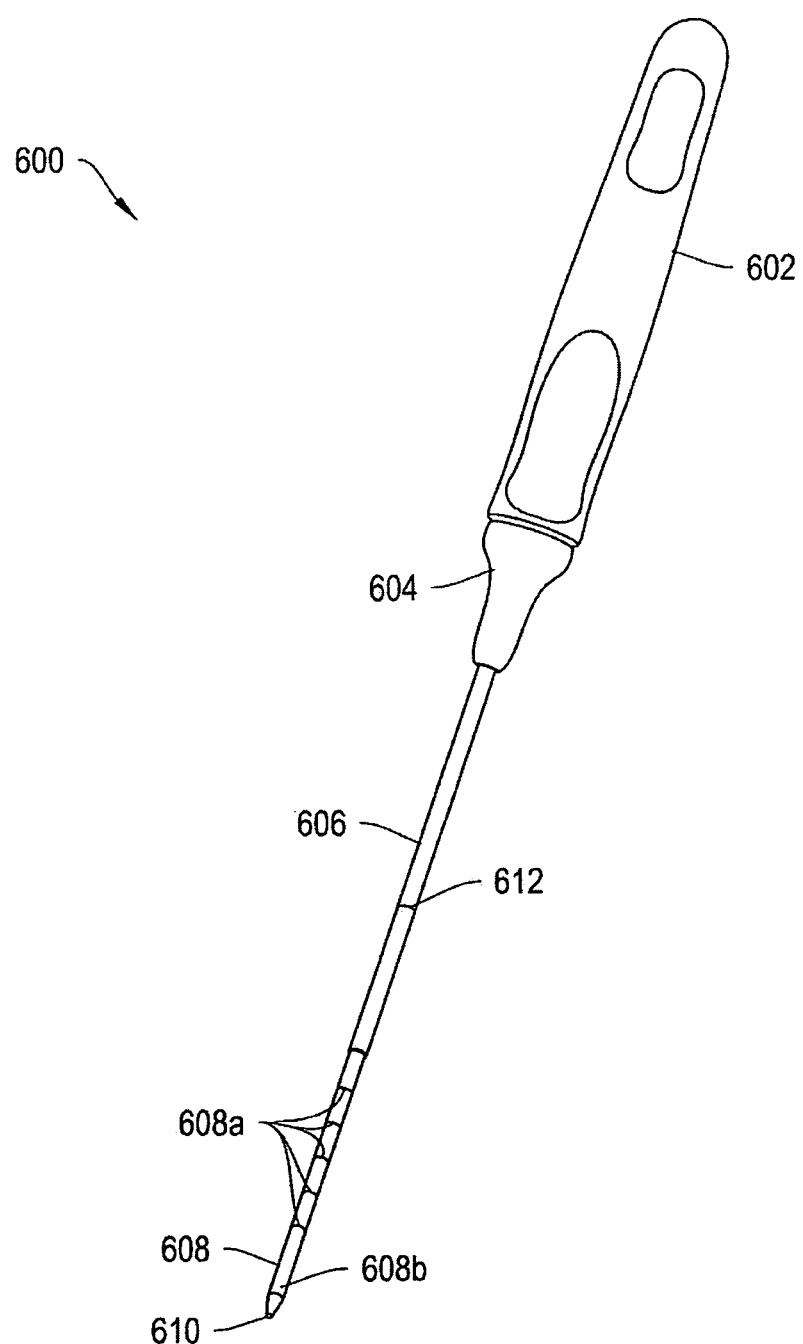
FIG. 22 depicts an exemplary delivery device that can be used to deliver an exemplary mesh to an anatomical location in the body of a patient.

FIG. 22 shows a delivery device 600 that can be used to deliver any of the exemplary meshes disclosed herein to an implantation location. The delivery device 600 includes a handle 602, a needle/shaft 608 extending distally from the handle 602, a pusher button 604 distal to the handle 602, and a cannula 606 disposed about the shaft 608 and extending distally from the pusher button 604.

The shaft 608 is generally linear at its proximal end 608a, and curves towards its distal end 608b. However, in other embodiments the shaft 608 may be straight, may include any combination of curved sections and straight sections, and/or may extend into one, two or more planes. When inserting the delivery device 600 through a vaginal incision and towards an obturator membrane, a straight shaft may facilitate access for an operator to more posterior regions of an obturator membrane, whereas a shaft with more curvature may facilitate access to more anterior regions of an obturator membrane. In certain embodiments, the shaft may be shorter in length than the depicted shaft 608 which may provide an operator with better control. In certain embodiments, the shaft 608 has a diameter of between about 0.075 inches and about 0.2 inches, and in certain embodiments is about 0.107 inches. The shaft 608 includes a tip 610. The tip 610 can be sharp and suited to incise and/or dissect human tissue, or blunt and suited for blunt dissection and/or dilation of human tissue. In certain embodiments, the tip is blunt so as to avoid damaging sensitive structures such as organs, nerves, and arteries, as will be discussed below.

The pusher button 604 comprises polymeric materials and is mechanically coupled to the cannula 606. The cannula 606 is shorter in length than the shaft 608, and when the button 604 is in a retracted state, as depicted in FIG. 22, the shaft 608 is exposed at its distal end. In certain implementations, the exposed portion of the shaft 608 is slightly longer than about half the length of the mesh so that the mesh remains external to the body during initial placement of the shaft 608.

The mesh can be coupled to any of the anchors described herein. The coupled anchors include respective axial through holes. The inner diameter of the anchor is preferably sized and shaped to fit around and slide against the outer diameter of the shaft 608. The anchor slides proximally along the shaft 608 and abuts the distal end of the pusher cannula 606. The outer diameter of the anchor can be smaller, larger, or equal to the outer diameter of the pusher cannula 606. The mesh can further include a center mark in a center region of the mesh that indicates the center, or "half-length," of the mesh. In one usage of device 600, the center mark of the mesh is placed directly underneath the urethra. However, in other implementations, device 600 is used with larger meshes that include marks which are placed under other anatomical structures, such as, for example, the base of the bladder.

The cannula 606 includes a pusher mark 612 that indicates where the center mark of the mesh will be positioned after the mesh has been placed using the delivery device 600. In one exemplary mode of operation, when an operator delivers the mesh using the delivery device 600 with the pusher button 604 and the cannula 606 retracted, the operator positions the pusher mark 612 underneath the urethra such that when the operator advances the pusher, the center mark of the mesh lies about or directly underneath the urethra. However, in embodiments wherein implants include marks indicating placement of the implant with respect to another anatomical structure, such as the base of the bladder, the operator accordingly positions the pusher mark 612 underneath that anatomical structure.

In operation, an operator couples an anchor of the mesh to the shaft 608. The anchor slides proximally along the shaft 608 and abuts the distal end of the pusher cannula 606. The operator inserts the shaft 608 into the body of the patient and guides the tip 610 towards a target region while the button 604 is retracted. In certain implementations, the operator advances the tip past the target region. The operator optionally gauges his proximity to the target region by aligning the center mark with an anatomical landmark such as the urethra. The operator advances the button 604 distally, and thereby advances the distal end of the cannula 606 towards the tip 610 of the shaft 608. In certain implementations, the operator advances the anchor to a target region within the anatomy of the patient without pushing the anchor off of the shaft 608. Instead, after placement of the anchor, the operator retracts the device 600 in a retrograde direction, which decouples the anchor from the shaft 608.

In addition to the cannula mark 612, the device 600 may include other marks that guide the operator. In order to measure how far to advance the button 604 and cannula 606, in certain embodiments the shaft 608 includes increment/measurement markings 608a etched into the shaft 608. The operator can use the measurement markings to gauge the distance from the tip 610 of the shaft to the distal end of the cannula 606. The markings 608a can be disposed using other methods, such as disposing a biocompatible ink or stain on the shaft 608.

The exemplary meshes, anchors and delivery devices access target soft tissue regions, such as the obturator membranes, via single vaginal incisions. Exemplary surgical techniques for implanting the meshes disclosed herein will now be described. As illustrated herein, the procedure can be applied with meshes that are configured to support the urethra or bladderneck for the treatment of UI; meshes that have longer anterior-to-posterior widths for supporting the bladder, uterus, and/or other organs located within the patient's pelvic region; and meshes incorporating resilient strengthening members such as those described herein.

Figure 23:
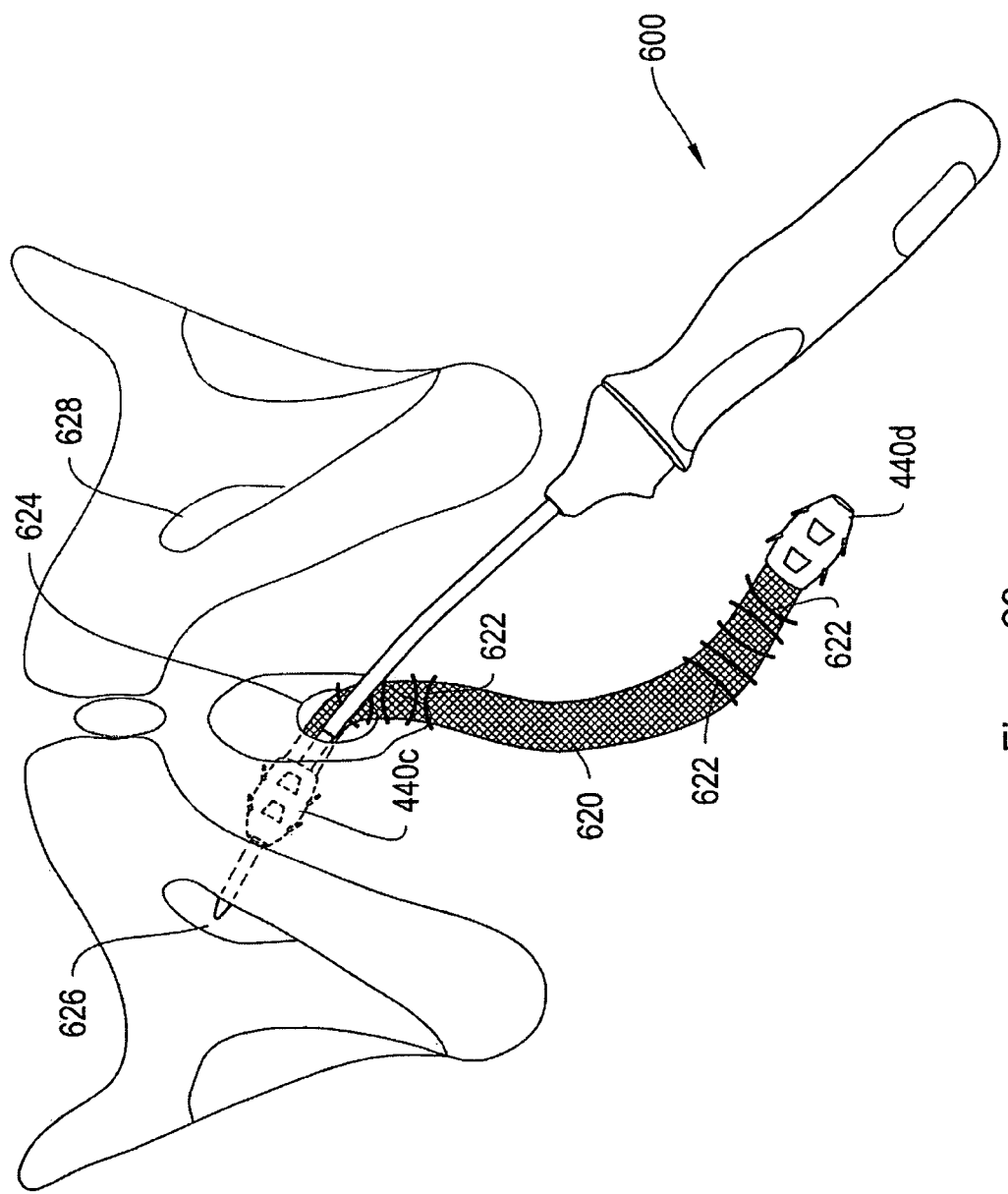
FIG. 23 illustrates an exemplary vaginal incision procedure that uses the delivery device of FIG. 22 to deliver an exemplary mesh.
Figure 24:
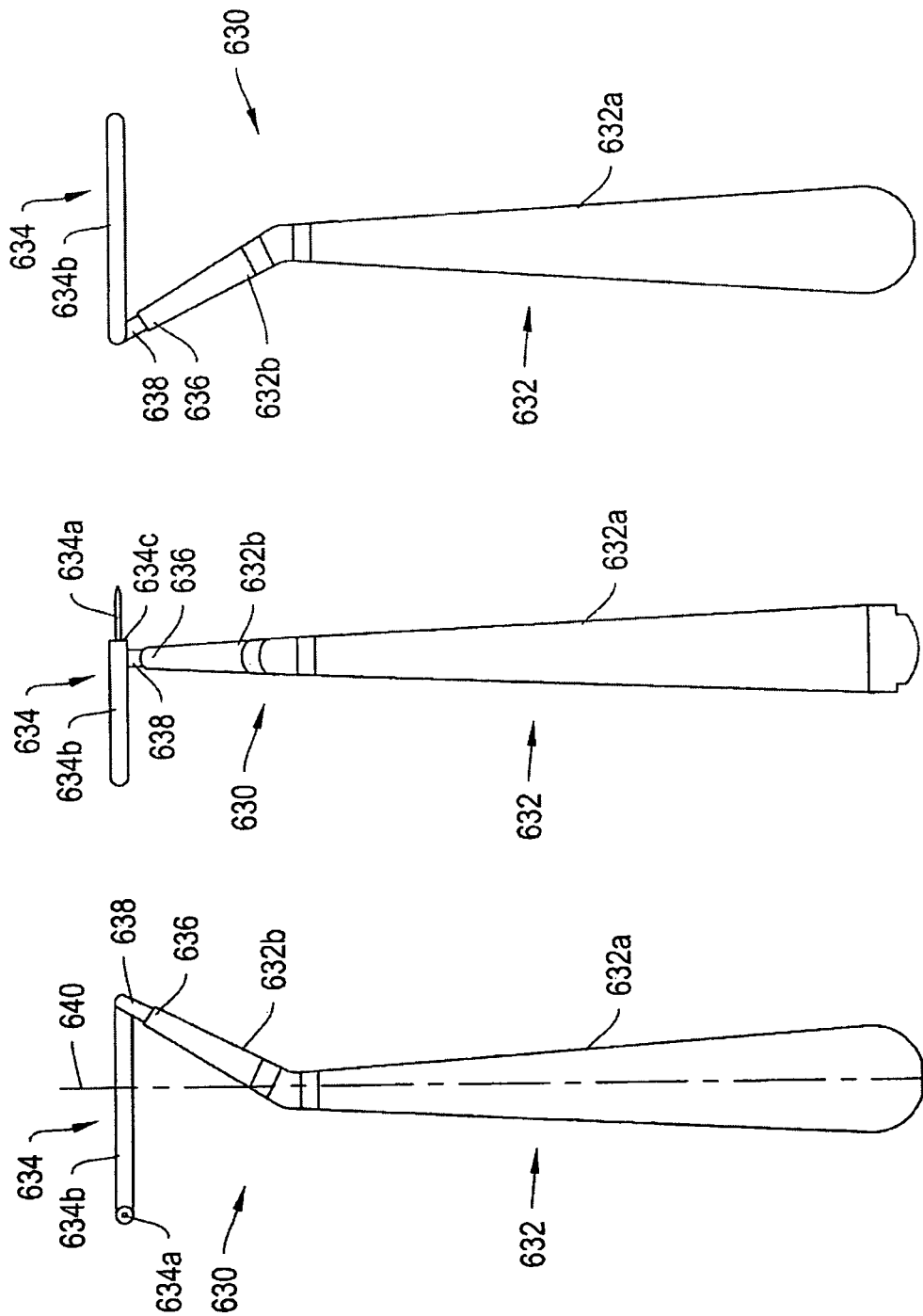
FIGS. 24A-24C depict an exemplary delivery device that can be used to deliver an exemplary mesh.

FIG. 23 illustrates an exemplary single vaginal incision procedure for using delivery device 600 to deliver an exemplary mesh 620 designed to underlie and support the urethra and/or bladderneck of the patient. The exemplary mesh 620 is similar to mesh 260 of FIG. 8, and in particular includes curved stiffening members 622 similar to members 268 of FIG. 8. The mesh 620 can be coupled to two soft tissue anchors 440c and 440d, one on each end of the mesh 620. The anchors 440c and 440d are similar to anchor 440 of FIG. 16A. The mesh 620 may also have one or more of any of the other strengthening members disclosed herein.

In the exemplary technique, the patient is placed on an operating table in a position to provide access to the pelvic region. The operator may subject the patient to local anesthesia, regional anesthesia, and/or general anesthesia or sedation according to his preference. Next, the operator makes a transverse incision (not shown) in the anterior vaginal wall of the patient and dissects the incision bilaterally according to his preference using, for example, surgical scissors. In certain implementations, the operator dissects bilaterally to the inferior pubic ramus on both sides of the patient. The operator then identifies a path of delivery of the implant by palpating tissue of the pelvic region. The operator may palpate by inserting his finger through the vaginal incision and may identify anatomical structures such as the obturator foramen.

Next, the operator accesses the patient's pelvic region via the single incision to insert the implant into the patient's pelvic region and secure the implant within the region so that at least a portion of the implant is located posterior to the bladderneck. To accomplish this, the operator first couples anchor 440c to the tip 610 of the shaft 608, inserts the distal end of the shaft 608 into the body through the external vaginal opening 624 and then guides the distal end of the shaft 608 through the vaginal incision towards an obturator membrane 626. The operator may palpate during delivery as preferred. The operator may also use the posterior portion of the patient's pubic bone as an anatomical landmark to assist in guiding the needle. The operator optionally secures the mesh 620 against the shaft 608 during delivery so that the mesh 620 does not obstruct the operator's vision or the path of delivery using any suitable sterile securing means, such as a sterile elastic band or tie.

The operator then punctures the obturator membrane 626 with the tip 610 but stops short of extending a portion of the tip 610 or shaft 608 through the surface of the patient's skin in the groin. The location of the puncture within the obturator membrane 626 depends on the location of the organ being supported. In certain implementations, the operator generally delivers the mesh 620 along a path that avoids certain pelvic structures, such as the internal pudendal artery, the pudendal canal, the perineal nerve, the labial nerve, and other vascular and nerve structures.

The operator may hear and/or feel a pop indicating that he has pierced the obturator membrane 626. The operator gauges the length from the vaginal incision to the obturator 626 by using the markings or indications (not shown) on the shaft 608, by using the mark 612 (not shown in this figure) on the cannula 606, and/or by visually gauging the length from the proximal edge of the anchor 440c to the vaginal incision to assure that the length of the mesh 620 is suitable for the patient. As mentioned above, in certain implementations, the mesh 620 includes a visual marking that the operator places under a predetermined anatomical landmark, such as the urethra or the bladder.

If needed, the operator further advances the shaft 608 to be near, contact, apply pressure to, poke ("tent-up"), or, in certain uses, pierce the epidermis (not shown) just beyond the obturator membrane 626, without penetrating entirely through the skin, until the shaft 608 is in an appropriate position to deliver the anchor 440c. The operator may externally palpate the epidermis proximal to the obturator membrane to feel the shaft 608 poke the epidermis and confirm its location. In certain embodiments the operator stops extending the tip 610 when it reaches a position that is beneath the patient's stratum corneum, while in other embodiments the operator stops the tip 610 from extending to the epidermis. In certain embodiments the operator stops the tip 610 in the subcutaneous tissue or beneath the subcutaneous and does not extend the tip 610 to the dermal layer In certain implementations, the incision is made in the vagina so as to allow the inserted shaft to be near, contact, apply pressure to, or poke the skin at a position that is generally in line with the urethral meatus. The operator anchors the anchor 440c to the obturator membrane, and retracts the shaft 608, thereby decoupling the shaft 608 from the anchor 440c, using methods discussed above.

The operator repeats the process on the contralateral side, delivering anchors 440d to the obturator membrane 628 through the same vaginal incision. The operator also inserts a center region of the mesh 620 through the vaginal incision. In certain implementations the center region is inserted after the operator inserts the anchor 440c on one side of the patient but before inserting anchor 440d on the other side. Once all of the anchors 440c and 440d are delivered through the vaginal incision in the anterior vaginal wall and extended to respective obturator membranes 626 and 628, the entire mesh 620 will have been delivered through the vaginal opening 624 and through the vaginal incision, and thus lie in a region anterior to the vaginal canal and supporting the urethra, bladder, and/or bladderneck.

Although cystoscopies are not required with the above-described procedure, the operator may perform a cystoscopy to check for bladder damage after delivering any or all of the anchors. Also during delivery, the operator optionally uses a pair of forceps or another suitable medical instrument to space the mesh 620 from the urethra (not shown) during delivery of one or more of the anchors to prevent excessive tension or stress on the urethra. When completed, the operator reviews the mesh 620 to confirm that it is properly placed under the organ needing support, then sutures the vaginal incision.

For certain patients, the lateral length of the mesh 620 may be longer than the obturator-to-obturator length of that patient. In these cases, the operator may leave equal lengths of the implant displaced on external sides of the obturator membranes 626 and 628. By way of example, if the mesh 620 has a lateral length of about 10 cm, then the patient with obturator to obturator length of about 7 cm will have about 1.5 cm of implant displaced on each side beyond the obturator membranes 626 and 628. Alternately, the manufacturer can supply implants with various lateral lengths to suit various patients. The device 600 and a similar delivery technique can be used to deliver meshes that are instead sized and shaped for treating pelvic floor disorders.

The surgical methods described above are non-limiting examples. Others will be apparent upon review of this disclosure. In certain alternative implementations, devices used to insert the implants are set forth in FIGS. 24A-24C. In particular, FIGS. 24A-24C show another illustrative delivery device 630 that is sized and shaped for transobtural placement of an implantable implant through the single vaginal incision, and employable, without limitation, with any of the illustrative embodiments described herein. More particularly, the delivery device 630 includes a handle 632 with first 632a and second 632b substantially straight sections located substantially in a first plane and angled relative to each other, a transitional portion 638 extending out of a distal end 636 of the handle 632 which interfits and extends axially out of the distal end 636 of the second straight handle section 632b, and a halo-shaped curved shaft 634 extending from a distal end of the transitional portion 638. The curved shaft 634 includes a reduced diameter section 634a at a distal end of the shaft 634 and an increased diameter section 634b at a proximal end of the shaft 634. The increased diameter section 634b and the reduced diameter section 634a adjoin to form a shoulder/ledge 634c. In use, an operator couples a soft tissue anchor to the device 630 by interfitting the reduced diameter section 634a of the shaft 634 through a through-aperture of the soft tissue anchor. The increased diameter section 634 should have a cross-section with a larger diameter than the diameter of the through-aperture, and thus the shoulder 634c provides a mechanical stop that prevents the anchor from sliding proximally along the shaft 634. In certain embodiments, the increased diameter section 634b and the reduced diameter section 634a are manufactured from a unitary body. However, in other embodiments, the increased diameter section comprises a flexible sheath or covering that an operator slides over the reduced diameter section 634a and around the shaft 634.

In this embodiment, the first substantially straight section 632a has a longitudinal axis 640 that is normal to the plane of the curved shaft 634. However, the longitudinal axis 640 can form any suitable angle with respect to the plane of the curved shaft (e.g., about 10, 20, 30, 45, 60, 70 or 80 degrees). By way of example, a device similar to device 630 of FIGS. 24A-24C can have alternative flat handles, tapered tips at distal ends of the curved shafts, and longitudinal axes that form angles of about 60 degrees with respect to the planes of the curved shafts.

Figure 25:
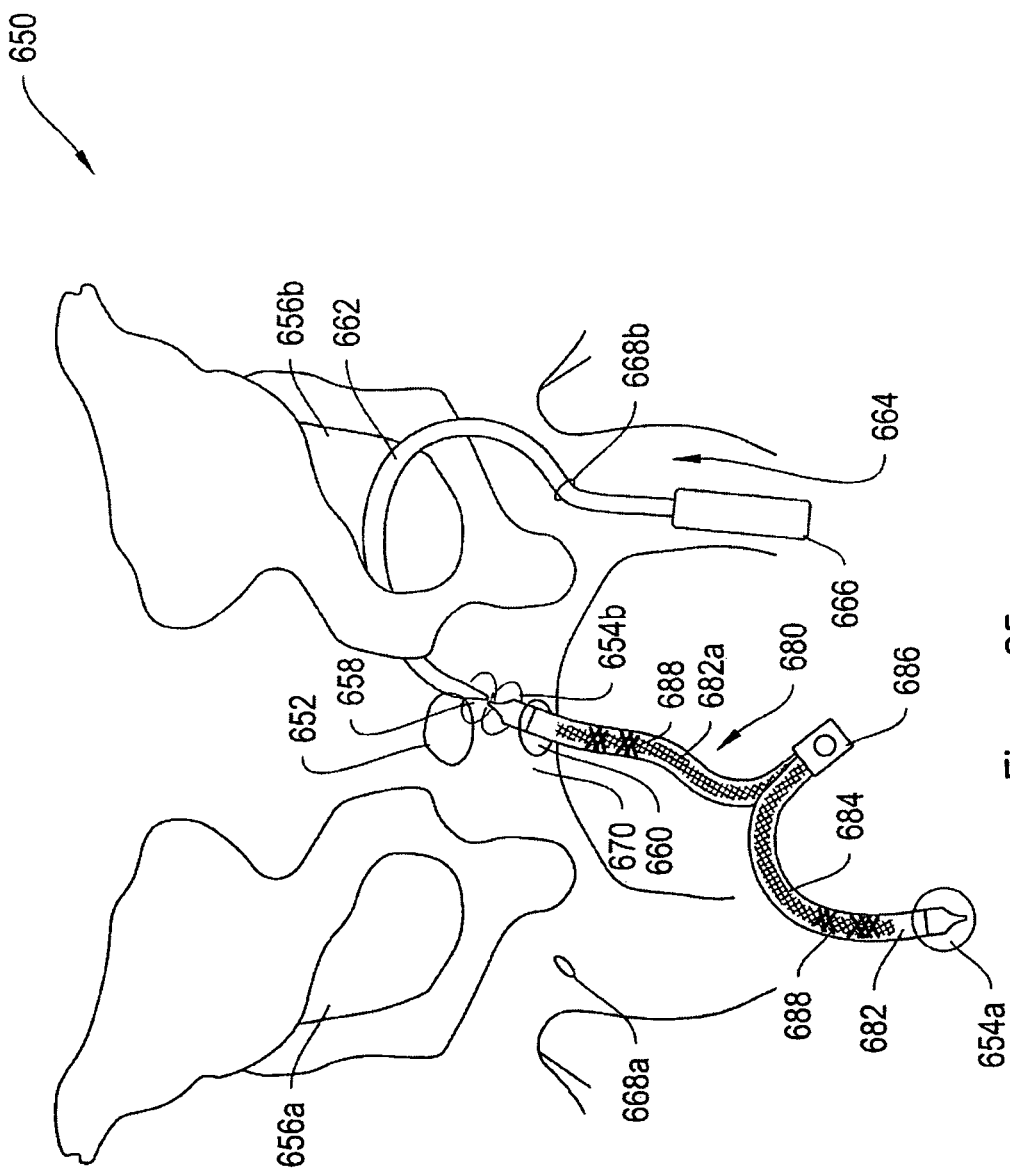
FIG. 25 illustrates an exemplary transobturator approach for delivering an exemplary mesh to an anatomical location in the body of a patient.

Described now with respect to FIG. 25 is another illustrative method for delivering a mesh to an anatomical site in the body of a patient. The mesh can incorporate any of the resilient strengthening members disclosed herein, such as straight stiffening members 688, which are shown arrayed in overlapping X structures similar to mesh 180 of FIG. 4B. The illustrative method includes an outside-in trans-obturator approach.

A first incision 668b is made on the inside of the patient's thigh, for example, about 1 cm outside the external margin of the labia majora. The operator inserts the shaft 662 of the delivery device 664, tip first, into the first incision 668b and continues to penetrate a first obturator foramen 656b. With a rotating wrist motion, the shaft 662 is guided along the posterior ischiopubic ramus to a vaginal incision 660 on the vaginal wall 670. After a distal portion 658 of the shaft 662 emerges out of the vaginal wall 670, the operator associates a distal end of the shaft 662 with a first end of a mesh assembly 680.

According to one illustrative embodiment, the distal end of the shaft 662 includes an L-slot onto which an association loop located at the first end of the mesh assembly may be hooked. More particularly, a first association loop is slid over the distal end 658 of the shaft 662 of the delivery device and radially into a first channel. The association loop is then moved distally away from the delivery device within a second channel to hook one end of the mesh assembly onto the delivery device. The delivery device is then withdrawn from the ishiopubic incision, drawing the end of the sling assembly through the passage created by the shaft 662. The orientation of the L-slot with respect to the ishiopubic approach ensures that the association loop is tensioned toward the closed, distal end of the L-slot as the delivery device is withdrawn. Subsequent to withdrawal, the association loop and the distal end 658 of the shaft 662 are oriented perpendicularly to each other, and then the association loop is unhooked from the delivery device.

The process can then be repeated with the same or a second delivery device on the contralateral side of the body with a second association loop, such as the association loop of the mesh assembly 680. Optionally, a single cystoscopy may be performed with two delivery devices in place, prior to withdrawal of the delivery devices to verify integrity of the bladder. Cystoscopy could also be performed, as desired, after each placement of a delivery device on a side of the body.

In an alternative approach, a guide, such as the dilator tubes 590a and 590b of FIG. 21, extends from each sling assembly end 654a and 654b. The dilator tube can be slid over the distal end 658 of the shaft 662. Then, the operator withdraws the shaft 662 of the delivery device back out of the obturator foramen 656b, bringing the sleeve end of the sling assembly 680 out of the first thigh incision 668b.

Once again, the process can then be repeated with the same or a second delivery device on the contralateral side of the body with a second dilator tube. Optionally, a single cystoscopy may be performed with two delivery devices in place, prior to withdrawal of the delivery devices to verify integrity of the bladder. Cystoscopy may also be performed, as desired, after each placement of a delivery device on a side of the body. Once desired placement of the sling assembly is achieved, the tabbed spacer 686 is cut. Then, by pulling on the guides or dilator tubes, as the case may be, the medical operator can slide the sleeve 682a off the sling 684 and remove it from the body. The delivery device(s) and the plastic sleeve 682a, including the guides or the dilator tubes, as the case may be, may then be discarded. In some embodiments the sling ends are anchored or otherwise affixed to muscle, tissue, or bone within the pelvic region of the body using stiffening members 688.

Figure 26A:
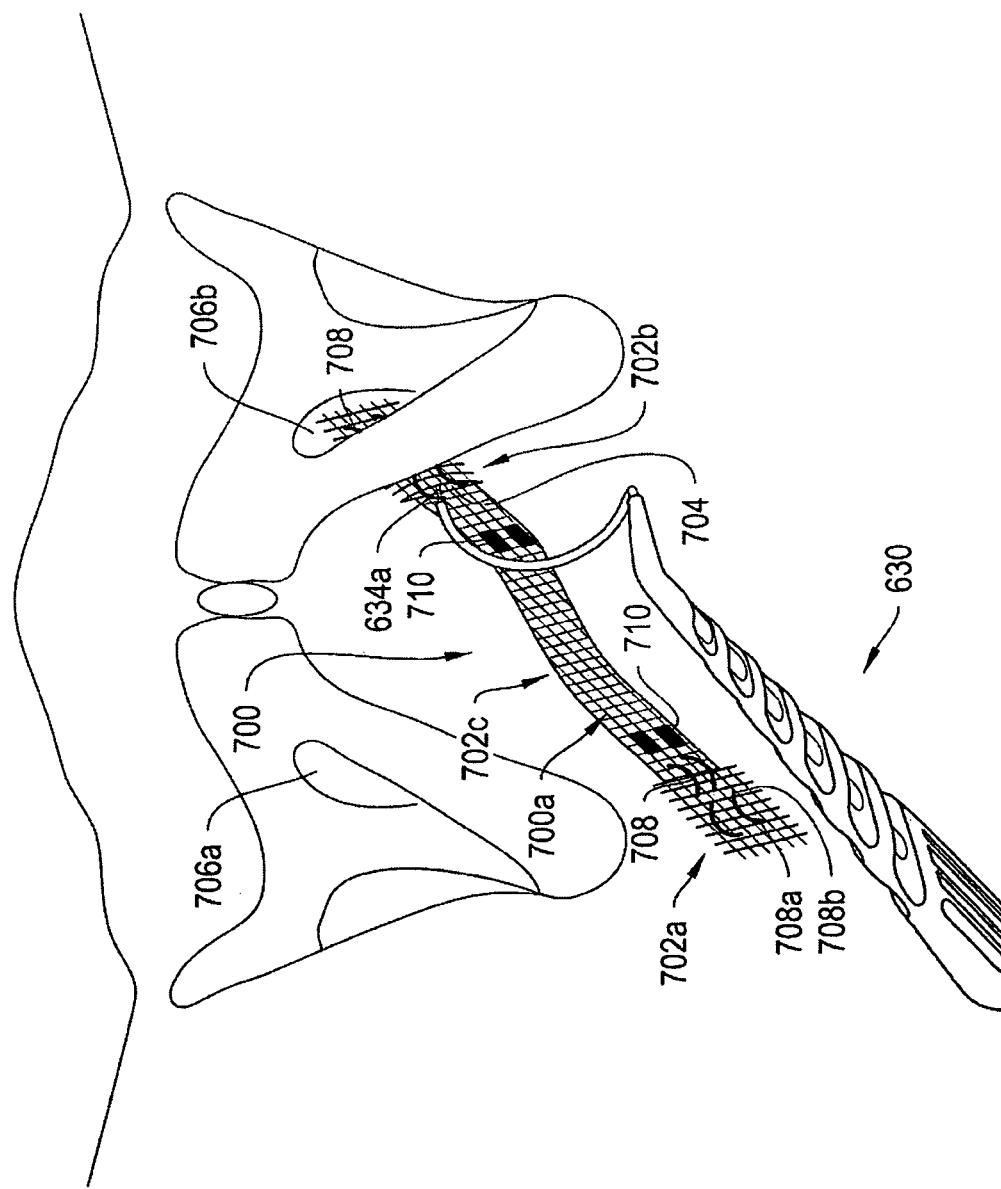
FIGS. 26A and 26B illustrate an exemplary transobturator approach using the delivery device of FIGS. 24A-24C to delivery exemplary meshes.
Figure 26B:
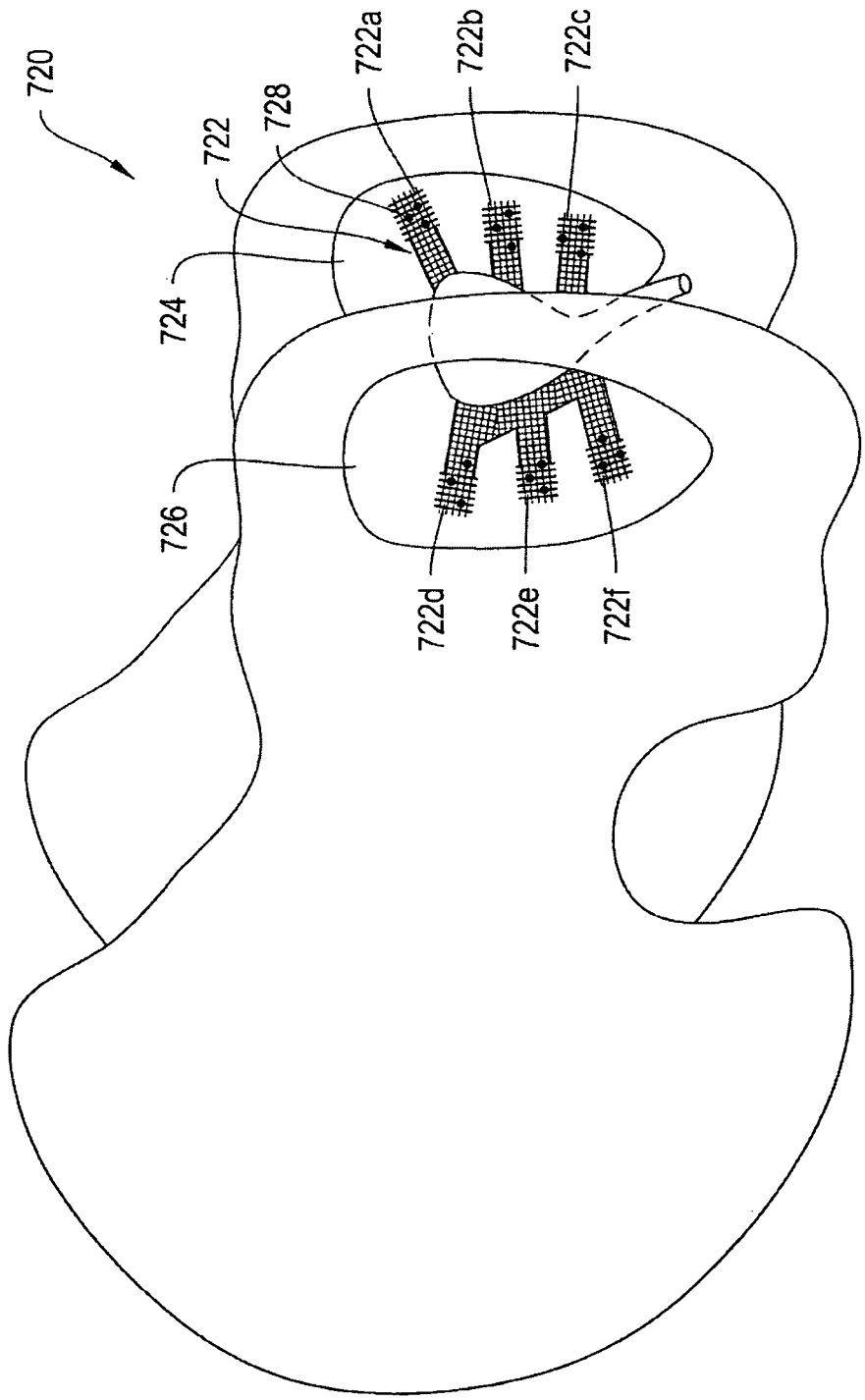

FIGS. 26A and 26B depict an illustrative inside-out transobtural method for delivering an exemplary mesh to an implantation location. FIG. 26A depicts a mesh 700 directly coupled to the delivery device 630 that was shown in FIGS. 24A-24C. The mesh 700 includes tanged portions 702a and 702b at respective ends of the implant 700, and a non-tanged portion 702c between the tanged portions 702a and 702b. The mesh 700 can also incorporate resilient strengthening members, such as curved stiffening members 708, arrayed similarly to curved stiffening members 286 of FIGS. 9A and 9B, and strengthening bars 710, arrayed similarly to strengthening bars 430 of FIGS. 15A and 15B. The curved stiffening members 708 each have protrusions 708a and 708b formed along both top 100a on bottom (not shown) surfaces of the mesh 700 within regions of the tanged portions 702a and 702b. This arrangement advantageously has protrusions in end regions of the mesh 700 along both longitudinal surfaces and both longitudinal edges to help secure the end regions within the patient's tissue, which may obviate the need for an anchor. The mesh 700 may also have one or more of any of the other strengthening members disclosed herein.

In use, the operator couples the implant 700 directly to the delivery device 630 by sliding the reduced diameter portion 634a through one of the holes 704 of the mesh 700. In order for the reduced diameter portion 634a to fit through one of the interstices, in certain embodiments the reduced diameter portion 634a has a diameter of less than about 1 mm. The operator then guides the distal end of the delivery device 630 to the obturator membrane 706b. However, instead of piercing a soft tissue anchor through the obturator membrane, the operator drives the reduced diameter portion 634a of the device 630 with at least part of the tanged portion 702b having stiffening members 708 through the obturator membrane 706b. The delivery device 630 is then withdrawn through the vaginal incision leaving the tanged portion 702b implanted in or through the obturator membrane 706b. The operator then repeats this process to anchor the contra-lateral tanged portion 702a to the contra-lateral obturator membrane 706a.

The tanged mesh 700 is sized and shaped to treat urinary incontinence by supporting the patient's urethra and/or bladderneck. Tanged meshes incorporating strengthening members can also be used for treating other pelvic floor disorders. FIG. 26B shows an oblique view of the pelvic region 720 of a patient with a mesh 722 similar to the implant 520 of FIG. 18, but having tanged straps 722a-f incorporating retention nodules 728 similar to retention nodules 428 of FIG. 15. Similarly to the strengthening members 708 of FIG. 26A, the nodules 728 protrude along longitudinal surfaces of the tanged straps 722a-f. This arrangement advantageously has protrusions in end regions of the mesh 720 along both longitudinal surfaces and both longitudinal edges to help secure the end regions within the patient's tissue, which may obviate the need for anchors. The mesh 700 may also have one or more of any of the other strengthening members disclosed herein. To deliver the mesh 722, the operator uses a similar method as that described in connection with FIG. 26A to deliver each of the tanged ends 722a-c to a first obturator membrane 724 and to then deliver each of the tanged straps 722d-f to a contralateral obturator membrane 726.

After placing a surgical implant, the operator may tension the implant to provide the proper support to anatomical structures of the pelvic region using methods described above.

In addition to the obturator membranes, in certain alternative implementations an operator may elect to anchor the implant to other anatomical structures. These structures include posterior or lateral tissues or muscles, such as the sacrospinous ligament and the levator ani muscle. The sacrospinous ligament is a thin and triangular tissue that is attached by its apex to the spine of the patient's ischium, and medially, by its broad base, to the lateral margins of the sacrum and coccyx in front of the sacrotuberous ligament. The sacrospinous ligament is a convenient location to anchor mesh straps in the posterior regions of the pelvic floor in order to provide posterior support. The levator ani muscle is a broad, thin muscle situated generally on the side of the pelvis that is attached to the inner surface of the lesser pelvis. It is a convenient location to anchor mesh straps in order to provide lateral and/or posterior support and tension for a surgical implant.

The resilient strengthening members described herein, including the exemplary stiffening members, fibers, retention nodules, strengthening bars, and anchors, are configured from synthetic materials, non-synthetic materials, or both. In certain embodiments, the resilient strengthening members are biodegradable, either in whole or in part, and such embodiments may employ any of the materials referenced herein. The resilient strengthening members may be made from biocompatible metals, composites, plastics or other polymeric materials. Examples of suitable metals include, but are not limited to, stainless steel, titanium, and alloys such as nickel-titanium of nitinol. Suitable polymers, which can be used as a coating on a metal, include but are not limited to, plastics such as polytetrafluoroethylene. Moreover, the resilient strengthening members may be prepared to include a protective coating or treatment, and may also be configured to contain an agent for release into the patient's tissues. Any resilient strengthening members described herein may incorporate any of the materials described herein.

The resilient strengthening members may be manufactured by any suitable approach, including extrusion, injection molding, or spinning. The resilient strengthening members may be also be formed by disposing onto the mesh (e.g., mesh 100 depicted in FIG. 1) a molten material which later solidifies to form the components. The disposed molten material may or may not penetrate an exterior surface of the mesh 100. The resilient strengthening members may also be attached to the mesh 100 by any other suitable method. For example, the resilient strengthening members may be glued, heat-bonded, fused, woven, or tied to the mesh 100.

The mesh described herein may be fabricated from any suitable material(s), preferably biocompatible materials, and may be non-biodegradable or biodegradable. The non-biodegradable portions of the mesh may be fabricated from any of a plurality of biocompatible materials, such as nylon, silicone, polyethylene, polyester, polyethylene, polyurethane, polypropylene, polyvinyl polymers, fluoropolymers, copolymers thereof, combinations thereof, or other suitable synthetic material(s). The biodegradable portions of the mesh 100 may be derived from mammalian tissue, synthetic materials, or a combination of mammalian tissue and synthetic material. According to some configurations, the biodegradable portions of the mesh 100 are formed from synthetic polymers, such as polylactic acid, polyglycolic acid, or natural polymers, such as collagen, cellulose, polypeptides, polysaccharides, or copolymers thereof. According to some configurations, bioactive compounds may be added to the biodegradable polymers to enhance acute inflammation and encourage scar tissue formation. Examples of these inflammation promoters are fibrinogen and fibrin. The mesh 100 may incorporate or be coated with one or more agents to provide a therapeutic effect, for example, to reduce discomfort, to reduce the chance of infection, increase biocompatibility, and/or to promote tissue ingrowth. More examples of mesh materials are described below.

Exemplary mesh materials include, for example, synthetic materials, natural materials (e.g., biological) or a combination thereof. The non-degradable portion of the mesh may be fabricated from any of a number of non-degradable biocompatible materials, such as nylon, silicone, polyethylene, polyester, polyethylene, polyurethane, polypropylene, fluoropolymers, copolymers thereof, combinations thereof, or other suitable synthetic material(s). The biodegradable component of the mesh may be any suitable biodegradable material. The biodegradable material may be, for example, a biodegradable synthetic material. The term "biodegradable," is used synonymously with "bioabsorbable" and with "degradable" herein, and refers to the property of a material that dissolves in the body or is absorbed into the body. A mesh material may be fabricated from one or more yarns, which yarns may be made from one or more materials.

Suitable bioabsorbable synthetic materials include, without limitation, polylactic acid (PLA), polyglycolic acid (PGA), poly-L-lactic acid (PLLA), human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata.

Exemplary biodegradable polymers, which may be used to form a mesh, in addition to those listed above, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

In various implementations of the invention, the mesh, either as a whole or on a fiber by fiber basis, may include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the sling. The tissue growth factor may include natural and/or recombinant proteins for stimulating a tissue response so that collagenous tissue such as scar tissue growth is enhanced.

Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as *-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papavereturn, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfinuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocalne, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

In another aspect, the invention also includes methods of implanting a surgical mesh, such as the meshes described herein, within a patient for the treatment of urinary incontinence, pelvic floor prolapse, or both. In certain implementations, the meshes disclosed herein are adapted for implantation through transobtural, transabdominal, supra pubic, prepubic or other techniques. In certain implementations, the meshes may be inserted into the patient through a single vaginal incision surgical technique, such as the techniques disclosed in U.S. application Ser. No. 11/400,111, and entitled "Systems, Devices and Methods for Treating Pelvic Floor Disorders," filed Apr. 6, 2006, the contents of which are hereby incorporated by reference in their entirety.

According to another feature, the implants of the invention may include any suitable end portions, such as tissue dilators, anchors, and association mechanisms for associating the sling with the delivery devices of the invention. They may also include other slings, sling assemblies, sling delivery approaches, sling assembly-to-delivery device association mechanisms, and sling anchoring mechanisms. These and other features with which the delivery devices, implants, methods, and kits of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,128, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," U.S. patent application Ser. No. 10/957,926, entitled "Systems and Methods for Delivering a Medical Implant to an Anatomical Location in a Patient," U.S. patent application Ser. No. 11/115,655, entitled "Surgical Implants and Related Methods," and U.S. patent application Ser. No. 11/399,913, entitled "Systems, Methods, and Devices for Sub-urethral Support." The entire contents of all cited references are incorporated herein by reference in their entirety.

The foregoing embodiments are merely examples of various configurations of the resilient strengthening members and meshes described and disclosed herein and are not to be understood as limiting in any way. Additional configurations can be readily deduced from the foregoing, including combinations thereof, and such configurations and combinations are included within the scope of the invention. Variations, modifications, and other implementations of what is described may be employed without departing from the spirit and the scope of the invention. More specifically, any of the method, system and device features described above or incorporated by reference may be combined with any other suitable method, system, or device features disclosed herein or incorporated by reference, and is within the scope of the contemplated inventions. The specifications and other disclosures in the patents, patent applications, and other references cited herein are hereby incorporated by reference in their entirety.

The invention claimed is:

1. An implant for use in treating a pelvic floor condition in a patient, the implant comprising:
   a mesh having a first longitudinal edge and a second longitudinal edge and at least one longitudinal surface and being sized and shaped to support one or more of a patient's urethra, bladderneck, and pelvic organ;
   a tissue anchor coupled with a proximal end of the mesh, the tissue anchor being configured to penetrate a tissue of the patient; and
   a resilient strengthening member woven into the mesh and spaced apart from the tissue anchor,
   the resilient strengthening member having a first end and a second end, the resilient strengthening member extending across a transverse width of the mesh, the first end of the resilient strengthening member protruding beyond the first longitudinal edge of the mesh and the second end of the resilient strengthening member protruding beyond the second longitudinal edge of the mesh.

2. The implant of claim 1, wherein the resilient strengthening member is attached to the mesh at a plurality of points.

3. The implant of claim 1, wherein the tissue is a first tissue and the resilient strengthening member is a rigid member having a portion adapted to penetrate a second tissue of the patient.

4. The implant of claim 3, wherein the rigid member is disposed substantially perpendicular to the first longitudinal edge.

5. The implant of claim 1, wherein the resilient strengthening member is disposed in an end region of the mesh.

6. The implant of claim 5, wherein the resilient strengthening member is distally disposed at about 25% of a way from the proximal end of the mesh to a center of the mesh.

7. The implant of claim 5, wherein the resilient strengthening member is spaced away from a center region of the mesh, the center region of the mesh being adapted to be adjacent to one or more of the patient's urethra, bladderneck, and pelvic organ.

8. The implant of claim 1, wherein the resilient strengthening member includes plastic or metal.

9. The implant of claim 1, further comprising a plurality of resilient strengthening members.

10. The implant of claim 9, further comprising a first plurality of resilient strengthening members disposed in a first end region of the mesh and a second plurality of resilient strengthening members disposed in a second end region of the mesh.

11. An implant for use in treating a pelvic floor condition in a patient, the implant comprising:
a mesh configured to support one or more of a patient's urethra, bladderneck, and pelvic organ, the mesh having a first longitudinal edge, a second longitudinal edge, a first end region, a second end region and a center region;
a first plurality of stiffening members woven into the mesh and disposed in the first end region of the mesh; and
a second plurality of stiffening members woven into the mesh and disposed in the second end region of the mesh, the center region of the mesh being devoid of stiffening members,
each stiffening member of the first plurality of stiffening members and the second plurality of stiffening members extending across a transverse width of the mesh and having a first end and a second end, the first end protruding beyond the first longitudinal edge of the mesh and the second end protruding beyond the second longitudinal edge of the mesh.

12. The implant of claim 11, wherein the first plurality of stiffening members are longitudinally arrayed in the first end region of the mesh.

13. The implant of claim 11, wherein the second plurality of stiffening members are longitudinally arrayed in the second end region of the mesh.

14. The implant of claim 11, wherein the stiffening members of the first plurality of stiffening members and the second plurality of stiffening members are perpendicular with the first longitudinal edge and perpendicular with the second longitudinal edge.

15. The implant of claim 11, wherein first ends and the second ends of the first plurality of stiffening members are configured to penetrate a flesh of a patient and to stimulate scar tissue ingrowth at the first end region.

16. The implant of claim 11, wherein first ends and the second ends of the second plurality of stiffening members are configured to penetrate a flesh of a patient and to stimulate scar tissue ingrowth at the second end region.

* * * * *